US006875775B2

(12) United States Patent
Södervall et al.

(10) Patent No.: US 6,875,775 B2
(45) Date of Patent: Apr. 5, 2005

(54) TRIPHENYLALKENE DERIVATIVES AND THEIR USE AS SELECTIVE ESTROGEN RECEPTOR MODULATORS

(75) Inventors: Marja-Liisa Södervall, Oulu (FI); Arja Kalapudas, Oulu (FI); Lauri Kangas, Lieto (FI); Risto Lammintausta, Turku (FI); Pirkko Härkönen, Turku (FI); Kalervo Väänänen, Turku (FI); Arto Karjalainen, Espoo (FI)

(73) Assignee: Hormos Medical Oy LTD, Turku (FI)

( * ) Notice: Subject to any disclaimer, the term of this patent is extended or adjusted under 35 U.S.C. 154(b) by 44 days.

(21) Appl. No.: 10/408,303

(22) Filed: Apr. 8, 2003

(65) Prior Publication Data

US 2003/0225130 A1 Dec. 4, 2003

Related U.S. Application Data

(62) Division of application No. 09/712,252, filed on Nov. 15, 2000, now Pat. No. 6,576,645.
(60) Provisional application No. 60/165,828, filed on Nov. 16, 1999.

(51) Int. Cl.$^7$ .................. A61K 31/445; A61K 31/415; C07D 233/00; C07D 211/21; C07D 211/32
(52) U.S. Cl. ............... 514/317; 514/331; 514/396; 514/428; 514/644; 514/648; 514/651; 514/720; 514/724; 546/192; 546/229; 546/232; 546/234; 546/236; 546/239; 546/240; 548/300.1; 548/515; 564/324
(58) Field of Search ............ 564/324; 548/575, 548/300.1; 546/192, 229, 252, 234, 236, 239, 240; 514/428, 651, 648, 644, 720, 724, 317, 396, 331

(56) References Cited

U.S. PATENT DOCUMENTS

| | | | |
|---|---|---|---|
| 4,536,516 A | 8/1985 | Harper et al. ............... 514/54 |
| 4,656,187 A | * 4/1987 | Black et al. ............... 514/422 |
| 4,696,949 A | 9/1987 | Toivola et al. |
| 4,839,155 A | 6/1989 | McCague ............... 424/1.1 |
| 4,894,373 A | 1/1990 | Young |
| 4,996,225 A | 2/1991 | Toivola et al. |
| 5,118,667 A | 6/1992 | Adams et al. |
| 5,189,212 A | 2/1993 | Ruenitz |
| 5,192,525 A | 3/1993 | Yang et al. |
| 5,196,435 A | 3/1993 | Clemens et al. |
| 5,446,203 A | 8/1995 | McNelis |

(Continued)

FOREIGN PATENT DOCUMENTS

| | | |
|---|---|---|
| EP | 0 095 875 A2 | 12/1983 |
| GB | 1064629 | 4/1967 |
| WO | WO 92/06068 | 4/1992 |
| WO | WO 93/19746 | 10/1993 |
| WO | WO 95/26720 | 10/1995 |
| WO | WO 96/07402 | 3/1996 |
| WO | WO 96/35417 | 11/1996 |
| WO | WO 96/40616 | 12/1996 |
| WO | WO 97/32574 | 9/1997 |
| WO | 0 779 808 B1 | 8/1999 |
| WO | WO 99/42427 | 8/1999 |
| WO | WO 99/63974 | 12/1999 |

OTHER PUBLICATIONS

Budavari, S. et al., eds., *The Merck Index, Eleventh Edition*, p. 1430, No. 9039, Merck & Co., Inc., Rathway, NJ, USA (1989).

(Continued)

*Primary Examiner*—Alan L. Rotman
*Assistant Examiner*—Raymond Covington
(74) *Attorney, Agent, or Firm*—Sterne, Kessler, Goldstein & Fox P.L.L.C.

(57) ABSTRACT

The invention provides novel selective estrogen receptor modulator compounds of the general formula:

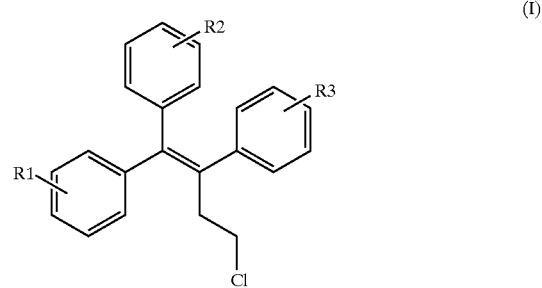

(I)

wherein R1 and R2, which are the same or different are a) H, halogen, OCH$_3$, OH; or b)

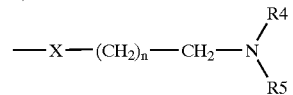

where X is O, NH or S; and n is an integer from 1 to 4; and R4 and R5, which are the same or different, are a 1 to 4 carbon alkyl, H, —CH$_2$C≡CH or —CH$_2$CH$_2$OH; or R4 and R5 form an N-containing five- or six-membered ring or heteroaromatic ring; or c) —Y—(CH$_2$)$_n$CH$_2$—O—R6
where Y is O, NH or S and n is an integer from 1 to 4; and R6 is H, —CH$_2$CH$_2$OH, or —CH$_2$CH$_2$Cl; or d) 2,3-dihydroxypropoxy, 2-methylsulfamylethoxy, 2-chloroethoxy, 1-ethyl-2-hydroxyethoxy, 2,2-diethyl-2-hydroxyethoxy or carboxymethoxy; and R3 is H, halogen, OH or —OCH$_3$;

stereoisomers thereof and their non-toxic pharmaceutically acceptable salts and esters and mixtures thereof, which compounds exhibit valuable pharmacological properties.

8 Claims, No Drawings

U.S. PATENT DOCUMENTS

| | | | |
|---|---|---|---|
| 5,470,883 A | | 11/1995 | Stromberg |
| 5,491,173 A | * | 2/1996 | Toivola et al. .............. 514/648 |
| 5,658,931 A | | 8/1997 | Bryant et al. |
| 5,691,355 A | | 11/1997 | Bryant et al. |
| 5,693,674 A | | 12/1997 | Bitonti |
| 5,719,136 A | | 2/1998 | Chwalisz et al. |
| 5,807,899 A | | 9/1998 | Bohlmann et al. |
| 5,821,254 A | | 10/1998 | Sporn et al. |
| 5,827,892 A | | 10/1998 | Löser et al. |
| 5,852,059 A | | 12/1998 | Thompson |
| 5,877,219 A | | 3/1999 | Willson |
| 5,912,273 A | * | 6/1999 | Degregorio et al. ........ 514/724 |
| 6,037,379 A | * | 3/2000 | Harkonen et al. ........... 514/721 |
| 6,576,645 B1 | * | 6/2003 | Sodervall et al. ........... 514/317 |

OTHER PUBLICATIONS

Goldstein, S.R. et al., "A pharmacological review of selective oestrogen receptor modulators," *Human Reproduction Update* 6:212–224, Oxford University Press (May–Jun. 2000).

Grodstein, F. and Stampfer, M.J., "Estrogen for women at varying risk of coronary disease," *Maturitas* 30:19–26, Elsevier Science Ireland Ltd. (Sep. 1998).

Henderson, V.W., "Estrogen, Cognition, and a Woman's Risk of Alzheimer's Disease," *The American Journal of Medicine* 103:115–185, Excerpta Medica, Inc. (1997).

Kangas, L. et al., "Bioluminescence of Cellular ATP: A New Method for Evaluating Cytotoxic Agents In Vitro," *Medical Biology* 62:338–343, Duodecim (1984).

Kangas, L. et al., "A new triphenylethylene compound, Fc–1157a: II. Anti effects," *Cancer Chemother. Pharmacol.* 17:109–113, Springer–Verlag (1986).

Kangas, L., "Biochemical and pharmacological effects of toremifene metabolites," *Cancer Chemother. Pharmacol.* 27:8–12, Springer–Verlag (1990).

Khovidhunkit, W. and Shoback, D.M., "Clinical Effects of Raloxifene Hydrochloride in Women," *Ann. Intern. Med.* 130:431–439, American College of Physicians (Mar. 1999).

Lobo, R.A., "Benefits and risks of estrogen replacement therapy," *Am. J. Obater. Gynecol.* 173:982–989, Mosby–Year Book, Inc. (1995).

Macgregor, J.I. and Jordan, V.C., "Basic Guide to the Mechanisms of Antiestrogen Action," *Pharmacol. Rev.* 50:151–196, Williams and Wilkins Co. (Jun. 1998).

Peng, Z. et al., "The Mechanical Strength of Bone in Different Rat Model: Experimental Osteoporosis," *Bone* 15:523–532, Elsevier Science Ltd. (1994).

Plouffe, L., "Selective Estrogen Receptor Modulators (SERMs) in Clinical Practice," *J. Soc. Gynecol. Investig.* 7:S38–S46, Elsevier Science Inc. (Jan.–Feb. 2000).

Qu, Q. et al., "Selective Estrogenic Effects of a Novel Triphenylethylene Compound, FC1271a, on Bone, Cholesterol Level, and Reproductive Tissues in Intact and Ovariectomized Rats," *Endocrinology* 141:809–820, Association for the Study of Internal Secretions (Feb. 2000).

Simberg, N.H. et al., "In Vitro and In Vitro Binding of Toremifene and Its Metabolites in Rat Uterus," *J. Steroid Biochem.* 36:197–202, Pergamon Press: plc (1990).

Terenius, L., "Structure–Activity Relationships of Anti–Oestrogens With Regard to Interaction with $17\mu$–Oestradol in the Mouse Uterus and Vagina," *Acta Endocrinol.* 66:431–447, Scandinavian University Press (1971).

International Search Report for corresponding International Application No. PCT/FI00/00946, mailed Feb. 8, 2001.

* cited by examiner

TRIPHENYLALKENE DERIVATIVES AND THEIR USE AS SELECTIVE ESTROGEN RECEPTOR MODULATORS

This is a divisional of U.S. patent application Ser. No. 09/712,252, filed Nov. 15, 2000 now U.S. Pat. No. 6,576,645, now allowed, which claims the benefit, under 35 U.S.C. §119(e), of the earlier filing date of U.S. provisional application, Appl. No. 60/165,828, filed on Nov. 16, 1999. The entirety of each of these applications is incorporated by reference herein.

FIELD OF INVENTION

This invention relates to triphenylalkene derivatives and their use as selective estrogen receptor modulators (SERMs).

BACKGROUND OF INVENTION

The publications and other materials used herein to illuminate the background of the invention, and in particular, cases to provide additional details respecting the practice are incorporated by reference.

Estrogens have been known as female sex hormones. However, lately many tissue-specific properties for estrogens have been described in organs, which are not classically considered to be estrogen-sensitive or estrogen-responsive. During the menopause the secretion of estrogens is dramatically decreased. Subsequently elderly women develop commonly climacteric symptoms including hot flushes, sweating, insomnia, depression, headache, vaginal dryness, cardiovascular symptoms, urinary incontinence, swelling feeling, breast tenderness and fatigue. In long-term estrogen deficiency induces cardiovascular disorders and osteoporosis which increase the risk of bone fractures and hospitalizations, which are very expensive to the society. Estrogens are increasingly used for the treatment of climacteric symptoms, but on the other hand estrogen use increases the risk of uterine and breast cancers (Lobo, 1995). Estrogens are shown to be beneficial also in the prevention of Alzheimer's disease (Henderson, 1997) and in the lowering of LDL-cholesterol values and thus preventing cardiovascular diseases (Grodstein & Stampfer, 1998). New therapies which would have the benefits of estrogens, but not the carcinogenic risks are requested. Selective estrogen receptor modulators (SERMs) have been developed to fulfill these requirements (Macgregor & Jordan, 1998). However, the presently used SERMs have properties which are far from optimal. E.g., raloxifen use is limited by its strong antiestrogenic properties, which cause and worsen the climacteric symptoms, although the effects on the bone are beneficial (Khovidhunkit & Shoback, 1999). It would be most desirable to develop tissue-specific estrogens, which could be used in women in the treatment of climacteric symptoms, osteoporosis, Alzheimer's disease and/or cardiovascular diseases without the carcinogenic risk. At the best new SERMs could be given to men to protect against osteoporosis, cardiovascular diseases and Alzheimer's disease without estrogenic adverse events (gynecomastia, decreased libido etc.).

OBJECT AND SUMMARY OF THE INVENTION

One object of the present invention is to provide novel selective estrogen receptor modulators.

Another object of the present invention is to provide a pharmaceutical composition comprising an amount effective to produce a tissue specific estrogenic and/or antiestrogenic effect of said novel selective estrogen receptor modulator compound, or a stereoisomer, or a non-toxic pharmaceutically acceptable salt or ester thereof, and a pharmaceutically compatible acceptable carrier therefor.

An additional object of the present invention is to provide a method of producing a tissue specific estrogenic and/or antiestrogenic effect in a subject in which such an effect is desired which comprises administering to said subject said novel selective estrogen receptor modulator compound, or a stereoisomer, or a non toxic pharmaceutically acceptable salt or ester thereof in an amount sufficient to produce the desired effect.

Thus, according to one aspect this invention concerns novel selective estrogen receptor modulator compounds of the general formula:

(I)

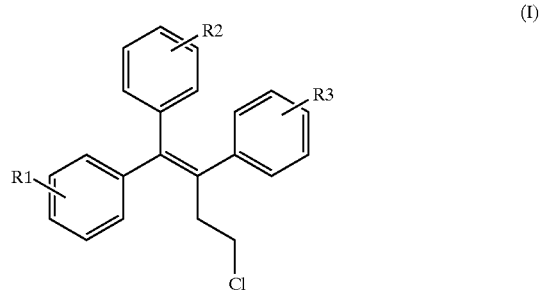

wherein R1 and R2, which are the same or different are a) H, halogen, $OCH_3$, OH; or b)

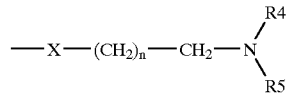

where X is O, NH or S; and n is an integer from 1 to 4; and

R4 and R5, which are the same or different, are a 1 to 4 carbon alkyl, H. —$CH_2C\equiv CH$ or —$CH_2CH_2OH$; or R4 and R5 form an N-containing five- or six-membered ring or heteroaromatic ring; or c) —Y—$(CH_2)_n CH_2$—O—R6 where Y is O, NH or S and n is an integer from 1 to 4; and

R6 is H, —$CH_2CH_2OH$, or —$CH_2CH_2Cl$; or d) 2,3-dihydroxypropoxy, 2-methylsulfamylethoxy, 2-chloroethoxy, 1-ethyl-2-hydroxyethoxy, 2,2-diethyl-2-hydroxyethoxy or carboxymethoxy; and R3 is H, halogen, OH or —$OCH_3$;

stereoisomers thereof and non-toxic pharmaceutically acceptable salts and esters and mixtures thereof, provided that a) when R2 is

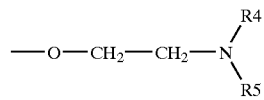

in the 4-position of the phenyl
where R4 and R5
i) are the same, either methyl or ethyl; or
ii) form an N-containing five-membered ring;
then R1 and R3 cannot simultaneously be H; and
b) when R2 is

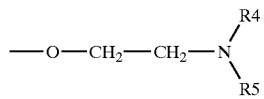

in the 4-position of the phenyl
where R4 and R5, which are the same or different, are methyl or H; or
when R2 is —O—CH$_2$CH$_2$—OH or —O—CH$_2$COOH in the 4-position of the phenyl, then R1 and R3, cannot simultaneously be H, or OH in the 4-position of the phenyl; and
if R1 is OH in the 4-position of the phenyl, R3 cannot be H.

According to another aspect the invention concerns a pharmaceutical composition comprising an amount effective to produce a tissue specific estrogenic and/or antiestrogenic effect of said novel selective estrogen receptor modulator compound, or a stereoisomer thereof, or a non-toxic pharmaceutically acceptable salt or ester thereof, and a pharmaceutically compatible acceptable carrier therefor.

According to an additional aspect the invention concerns a method of producing a tissue specific estrogenic and/or antiestrogenic effect in a subject in which such an effect is desired which comprises administering to said subject said novel selective estrogen receptor modulator compound, or a stereoisomer thereof, or a non-toxic pharmaceutically acceptable salt or ester thereof in an amount sufficient to produce the desired effect.

Additional embodiments and advantages of the invention will be set forth in part in the description as follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and not restrictive of the invention, as claimed.

DETAILED DESCRIPTION OF THE INVENTION

This invention relates to the use of novel selective estrogen receptor modulators (SERMs) and their pharmaceutical preparations in men and women for the treatment of degenerative diseases and symptoms due to estrogen deficiency. Typically SERMs act as estrogens in bone and cardiovascular system while they are antiestrogenic in breast tissue. SERMs may have agonistic and antagonistic effects in other tissues also. Depending on their chemical structure and hormonal properties some compounds can be especially suited for elderly women for the prevention of osteoporosis whereas others (which are not feminizing estrogens) may also be used in men in the prevention of osteoporosis, cardiovascular diseases and Alzheimer's disease. Some compounds are specifically suited for the treatment of climacteric symptoms in menopausal women. It is the common property of the described novel compounds that they are antiestrogenic in the mammary gland and inhibit the proliferation of breast cancer cells. They are also weak estrogens in the uterus and do not induce uterine cancers, the side effect of the well known SERM, tamoxifen. The new SERMs of the present invention thus have tissue-specific estrogenic and/or antiestrogenic effects in vitro and in vivo and are useful in the prevention and treatment of osteoporosis, cardiovascular diseases and Alzheimer's disease in men and women, as well as in the treatment of climacteric symptoms and breast cancer in women.

The compounds of formula (I) can be prepared by a process which comprises reaction of a compound of the formula

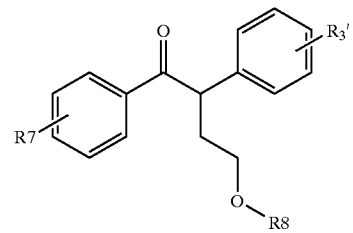

(II)

where R7 is the same as R1 or R2 as defined before or is a protected such group, R3' is R3 as defined before or a protected OH, R8 is benzyl or tetrahydropyranyl, with an organometallic compound of the formula

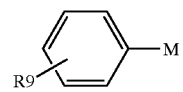

(III)

where R9 is H, R1 or R2 as defined before or is a protected such group and M is —Mg-halogen or Li, to give a compound of the formula

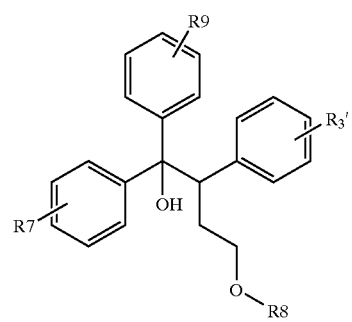

(IV)

where R$_3$', R7, R8, and R9 are as defined above, R8 is tetrahydropyranyl when R7 or R9 is —X—(CH$_2$)$_n$CH$_2$—OR6 where X and n are as defined in (I). The compound (IV) is dehydrated by an appropriate acid catalyst preferable with acetic anhydride/acetyl chloride to give a triphenylethylene derivative of the formula

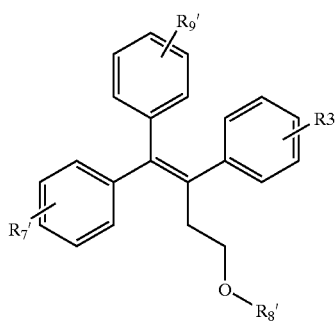

(V)

where R8' is H or benzyl, $R_7'$ and $R_9'$ are R1 and R2 or benzyl protected OH or benzyl protected —XCH$_2$CH$_2$OR6. The possible protecting tetrahydropyranrl groups in R3, R7, R8 and R9 are removed in this process to give radicals R3, $R_7'$, $R_8'$ and $R_9'$.

The removal of the possible benzylic $R_8'$ can be carried out by treatment with Zn and acetyl chloride in toluene to give the triphenylbutenol of the formula

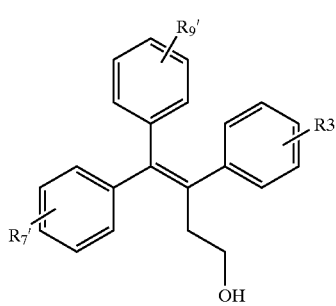

(VI)

The hydroxy compound (VI) can be converted to a corresponding chloride by treatment with thionyl chloride or with triphenyl phosphine-carbon tetrachloride in organic solvent to give the compound of the formula (VII)

The claimed compounds (I) are prepared from the compounds of the formula (VII) where $R_7'$ and/or $R_9'$ are benzyl protected —XCH$_2$CH$_2$OR6 by treatment with Zn and acetyl chloride in organic solvent or by catalytic hydrogenation.

Another process to prepare compounds of the formula (IV) is the hydroalumination reaction of a "styrene" derivative of the formula

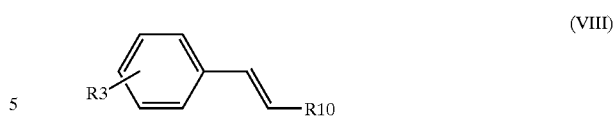

(VIII)

where R10 is —CHO, —CH$_2$OH, —COOH or a corresponding ester and R3 is as defined before with a benzophenone derivative of the formula

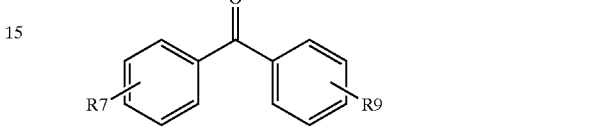

(IX)

Yet another process for the preparation of the compounds of the invention comprises O-alkylation of the compound of the formula (V) where $R_7'$ and/or $R_9'$ is OH with an alkyl halide derivative of the formula R11—(CH$_2$)$_m$-halogen (X)

where m is an integer from 1 to 5 and R11 is halogen, $$-N\begin{matrix}R4\\R5\end{matrix}$$

or —OR$_6'$ where R$_6'$ is R6 or protected R6, or —COOR to give a compound of the formula

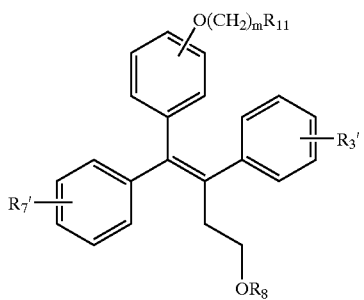

(XI)

The compound of the formula (XI) where R11 is halogen is reacted with an amine of the formula

to give a compound of the formula

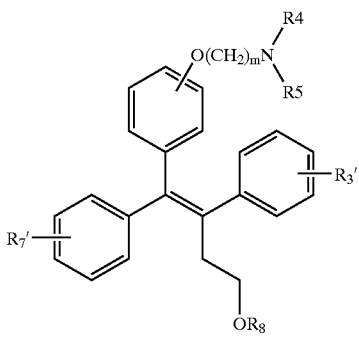

(XII)

Yet another process for the preparation of the compounds of the formula (VII) comprises the McMurry reaction of an benzophenone derivative of the formula

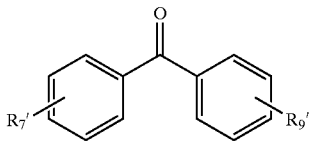

(XIII)

where $R_7'$ and $R_9'$ are as defined before, with an 3-chloropropiophenone derivative of the formula

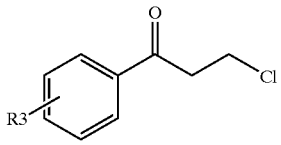

(XIV)

where R3 is as defined before.

The claimed compound of the formula (I) where R1 or R2 is 2,2-diethyl-2-hydroxyethoxy can be prepared by reaction of the compound of the formula (XI), where m is 1 and R11 is —COOR, with ethylmagnesium bromide.

The claimed compound of the formula (I) where R1 or R2 is 1-ethyl-2-hydroxyethoxy can be prepared by O-alkylation of the compound of the formula (V), where $R_7'$ or $R_9'$ is OH with ethyl α-bromobutyrate and by reduction of the formed ester by lithium aluminum hydride.

Compounds of formula (I) contain one or more asymmetric centers and may thus give rise to enantiomers, diastereomers and other stereoisomeric forms. The present invention is also meant to encompass racemic mixtures, resolved forms and mixtures thereof as well as the individual enantiomers that may be separated according to methods known to those of ordinary skill in the art.

The invention disclosed herein is also meant to encompass non-toxic pharmaceutically acceptable salts and esters of compounds of formula (I) and their stereoisomers. The non-toxic pharmaceutically acceptable salts and esters can be prepared by methods well-known to those of ordinary skill in the art. The non-toxic pharmaceutically acceptable salts include, but are not limited to, chlorides, bromides, sulfates, nitrates, phosphates, sulfonates, formates, tartrates, maleates, citrates, benzoates, salicylates, ascorbates and the like. The non-toxic pharmaceutically esters include, but are not limited to, methyl esters, ethyl esters, propyl esters, butyl esters and the like.

EXPERIMENTAL SECTION

Methods

Evaluation of Estrogenic and Antiestrogenic Properties of Compounds in MCF-7 Cell Growth Experiments in Vitro Estrogen-sensitive human breast cancer cells, MCF-7 (McGrath clone), were maintained in RPMI-1640 medium supplemented with 10% fetal calf serum, 2 mM L-glutamine, 10 μg/ml insulin and 10 μg/ml gentamicin. The cells were grown as monolayer cultures in 75 cm$^2$ plastic tissue culture flask (Nunc, Roskilde, DeiLark) in 25 ml medium at 37° C. in an atmosphere of 95% air, 5% $CO_2$ and subcultured twice a week.

For experiments involving hormone or anti-hormone treatment, the cells in exponential growth phase were precultivated in the absence of estradiol for one day. Cells were plated at a density of 3.5×10$^3$ cells/well in 96-well microtiter plates (Nunclon, Roskilde, Denmark) and incubated for 24 hours at 37° C, 95% air. 5% $CO_2$, RPMI-1640 medium (L-glutamine and gentamicin as above) with 5% stripped fetal calf serum (stripped twice with dextran-coated charcoal to remove the steroids) and without phenol red. After the incubation period the medium was removed. The exposure to study drugs was started immediately by adding fresh medium with 5% stripped serum. Half of the cells were grown with estradiol, half without estradiol. Study compounds (dissolved in ethanol in 0.01 M concentration and diluted with the growth medium as appropriate) were added. The final concentrations of the compounds were 1, 10, and 100 nM, and 1 and 10 μM. The cells were incubated for four days.

The amount of living cells was measured after 4 days by luminometer based on the amount of ATP and luciferase reaction as described by Kangas et al, 1984. This method allows evaluation of estrogenicity based on the ability of the compounds to stimulate the growth of the estrogen-dependent cells in the absence of estradiol.

Estrogenicity was estimated by comparing the maximal growth stimulus (at any concentration) of study compound as percent from growth stimulus by estradiol (100% stimulus). In the present studies antagonism was estimated at the concentration of 1 μmol/l as percent of theoretical full (100%) antagonism, which would mean complete inhibition of estradiol-stimulus. At high concentrations molecules may also show toxicity. Toxicity was estimated as the fraction of dead cells (i.e. 100% means that all cells have died during the exposure). The results are presented in Table 2.

Estimation of Estrogenicity and Antiestrogenicity in Vivo

The classical method to evaluate estrogenic and antiestrogenic effect is immature mouse or rat uterus (Terenius, 1971). The animals were exposed for 3 days to the compounds to be investigated at the age of 18 days. On the fourth day the animals were asphyxicated with $CO_2$ and body weight and uterine weight was recorded. Estrogens increase the size and weight of the uterus (uterotropic effect) while antiestrogens inhibit this action. The compounds are therefore given alone and with estradiol in order to evaluate both agonistic and antagonistic effects. The results have been shown in Table 3 both as per cent of estrogen stimulation (100%), and as inhibition of estrogen action (full inhibition is 100%). The values are given at two dose levels, low i.e. 3–5 mg/kg and high i.e. 10–50 mg/kg. Estrogenic activity can be estimated also after a 4 weeks' treatment of ovariectomized rats based on the uterine size. This assay was carried out in selected molecules as shown in Table 4.

Estimation of Effects to Cholesterol and Bone

Compounds were given p.o. to female rats for 4 or 5 weeks daily. At the end a blood sample was taken. Serum was separated by centrifugation and frozen until analyzed for total amount of cholesterol. Bone samples were taken from vertebra and tibia. Physical strength of the bones was studied as described by Peng et al, 1994. The assessments of the bone included:

Ash Weight of Tibial Epiphyses

Epiphyses of one tibia was carefully prepared and burned. Samples were burned to remove water and organic material. Ash weight relates to the mineral content of the bone. In addition, bone samples were taken to study the histomorphometry. In some cases the bone formation was studied by injecting tetracycline (50 mg/kg i.p. 10 days before autopsy) and calcein (20 mg/kg i.p. 3 days before autopsy). The method is based on permanent binding of tetracycline into growing bone and its detection by fluorescence (Peng et al, 1994).

Mechanical Testing of Bones

The mechanical testing of bones was carried out by materials testing machine, constructed in-house at Oulu University (Technical Services Department of the Medical Faculty). The testing machine is based on lever arm principle. One end of a steel lever is fixed. The pressing rod and the driving motor are connected to the lever arm with a moment ratio of 12.5 cm/50 cm=¼. As a driving motor a linear actuator (SEY 10 Magnetic Elektromotoren AG, Switzerland) is used to obtain constant vertical movement (0.62 cm/s). The interchangeable compression head is mounted on the pressing rod for different tests transmitting compressive force to the specimen, and moving at a constant speed of 0.155 mm/s up to a maximal load capacity of 1200 N. The pressing rod is guided via an axial ball bearing to keep the movement vertical. Compressive force is measured by a temperature-compensated force sensor, which is attached to the stationary part of the compression stage. The measuring electronics include sensor calibration and adjustments.

Strength of Femoral Neck

The maximal load on the femoral neck was measured by the cantilever bending test. The supporter for the bone was a thick polymethyl methacrylate plate in which several holes of different sizes were drilled. On one side of each hole a groove was engraved for the third trochanter of the femur. The femur was cut exactly between the middle and lower third of the shaft. The bone was inserted perpendicularly and tightly into a suitable hole on the supporter. The lesser trochanter of each bone touched the surface of the plate. This procedure allowed rapid and stable fixation of the bone without using any additional embedding materials. The concave compressing head, 2.5 mm in diameter, was made of aluminum. The femoral head-neck complex was tested until failure by loading the head with a force parallel to the shaft.

Estimation of Antitumor Activity in Vivo

Antitumor activity was estimated by using DMBA (dimethylbenz[a] anthracene) model. One single peroral dose of DMBA (12 mg) initiates mammary gland carcinogenesis. New compounds were administered for 5 weeks when palpable tumors appeared. Size of the tumors and number of new tumors were carefully estimated once a week until termination. The model has been described in detail by Kangas et al, 1986. The growth of the tumors was measured once a week. All tumors were classified according to their growth properties to progressing, stable and regressing ones. Disappeared tumors were separately calculated. The tumors were considered to be progressing, if the tumor volume grew more than 8-fold during the 5 weeks dosing period, and regressing if the tumor volume decreased to one fourth or less from the volume in the beginning. If tumor volume changed less or remained unchanged, the tumors were considered to be stable.

Results

Altogether 46 compounds were evaluated by the methods described above which are included in the list of example compounds numbered and listed in Table 1.

TABLE 1

Reference numbers (No.) and names of example compounds.

| No. | Compound |
|---|---|
| 1 | (E)-(2-{4-[4-Chloro-1-(4-fluorophenyl)-2-phenylbut-1-enyl]phenoxy }ethyl)-dimethylamine |
| 2 | (Z)-(2-{4-[4-Chloro-1-(4-fluorophenyl)-2-phenylbut-1-enyl]phenoxy}ethyl)-dimethylamine |
| 3 | (E)-(2-{4-[4-Chloro-1-(4-chlorophenyl)-2-phenylbut-1-enyl]phenoxy}ethyl)-dimethylamine |
| 4 | (E)-(2-{4-[4-Chloro-1,2-bis(4-chlorophenyl)but-1-enyl]phenoxy}ethyl)-dimethylamine |
| 5 | (Z)-(2-{4-[4-Chloro-1,2-bis(4-chlorophenyl)but-1-enyl]phenoxy}ethyl)-dimethylamine |
| 6 | (E)-4-Chloro-1-[4-(2-chloroethoxy)phenyl]-1,2-bis(4-chlorophenyl)-but-1-ene |
| 7 | (Z)-4-Chloro-1-[4-(2-chloroethoxy)phenyl]-1,2-bis(4-chlorophenyl)-but-1-ene |
| 8 | (E)-2-{4-[4-Chloro-2-phenyl-1-(4-fluorophenyl)but-1-enyl]phenoxy}ethanol |
| 9 | (E)-2-{4-[4-Chloro-1,2-bis(4-chlorophenyl)but-1-enyl]phenoxy}ethanol |
| 10 | (E)-3- {4- [4-Chloro-1-(4-chlorophenyl)-2-phenyl-but-1-enyl]phenoxy} propane-1,2-diol |
| 11 | (Z)-4-Chloro-1-[4-(2-methylsulfanyl-ethoxy)phenyl]-1,2-diphenyl-but-1-ene |
| 12 | (E)-{4-[4-Chloro-1-(4-chlorophenyl)-2-phenylbut-1-enyl]phenoxy}acetic acid |
| 13 | (Z)-{4-[4-Chloro-1-(4-chlorophenyl)-2-phenylbut-1-enyl]phenoxy}acetic acid |
| 14 | (E)-1-(4- {2-[(2-Chloroethoxy]ethoxy}phenyl)-4-chloro-1-(4-chloro-phenyl)-2-phenyl-but-1-ene |
| 15 | (E)-1-(4- {2-[(2-Chloroethoxy]ethoxy}phenyl)-4-chloro-1-(4-fluorophenyl)-2-phenyl-but-1-ene |
| 16 | 2-(4-{4-Chloro-1-[4-(2-hydroxyethoxy)phenyl]-2-phenyl-but-1-enyl}phenoxy) 1-ethanol |
| 17 | (E)-2-{4-[4-Chloro-2-phenyl-1-(4-chlorophenyl)but-1-enyl]phenoxy}ethanol |
| 18 | (Z)-2-[3-(4-Chloro-1,2-diphenyl-but-1-enyl)phenoxy]ethanol |
| 19 | (Z)-2-{2-[4-(4-Chloro-1,2-diphenylbut-1-enyl)phenoxy]ethoxy}ethanol |

TABLE 1-continued

Reference numbers (No.) and names of example compounds.

| No. | Compound |
|---|---|
| 20 | (Z)-3-[4-(4-Chloro-1,2-diphenyl-but-1-enyl)phenoxy]propane-1,2-diol |
| 21 | (Z)-1-{2-[4-(4-Chloro-1,2-diphenyl-but-1-enyl)phenoxy]ethyl}-1H-imidazole |
| 22 | (Z)-2-({2-[4-(4-Chloro-1,2-diphenyl-but-1-enyl)phenoxy]ethyl}methylamino)ethanol |
| 23 | (Z)-(2-{4-[4-Chloro-2-(4-chlorophenyl)-1-phenylbut-1-enyl]phenoxy}ethyl)-dimethylamine |
| 24 | (E)-(2-{4-[4-Chloro-2-(4-chlorophenyl)-1-phenylbut-1-enyl]phenoxy}ethyl)-dimethylamine |
| 25 | (Z)-(2-{4-[4-Chloro-2-(4-fluorophenyl)-1-phenylbut-1-enyl]phenoxy}ethyl)-dimethylamine |
| 26 | (Z)-(2-{4-[4-Chloro-2-(4-chlorophenyl)-1-(4-methoxyphenyl)but-1-enyl]phenoxy}-ethyl)dimethylamine |
| 27 | (E)-(2-{4-[4-Chloro-2-(4-chlorophenyl)-1-(4-methoxyphenyl)but-1-enyl]phenoxy}-ethyl)dimethylamine |
| 28 | (Z)-1-(2-{4-[4-Chloro-2-(3-methoxyphenyl)-1-phenylbut-1-enyl]phenoxy}-ethyl)piperidine |
| 29 | (E)-1-(2-{4-[4-Chloro-2-(3-methoxyphenyl)-1-phenylbut-1-enyl]phenoxy}-ethyl)piperidine |
| 30 | (Z)-1-(2-{4-[4-Chloro-2-(2-methoxyphenyl)-1-phenylbut-1-enyl]phenoxy}-ethyl)piperidine |
| 31 | (E)-1-(2-{4-[4-Chloro-2-(2-methoxyphenyl)-1-phenylbut-1-enyl]phenoxy}-ethyl)piperidine |
| 32 | (Z)-1-[4-(2-Dimethylaminoethylsulfanyl)phenyl]-1,2-diphenyl-4-chloro-but-1-ene |
| 33 | (Z)-{2-[3-(4-Chloro-1,2-diphenylbut-1-enyl)phenoxy]ethyl}dimethylamine |
| 34 | (E)-3-{4-Chloro-1-[4-(2-hydroxyethoxy)phenyl]-2-phenyl-but-1-enyl}-phenol |
| 35 | (Z)-3-[4-(4-Chloro-1,2-diphenylbut-1-enyl)phenoxy]propan-1-ol |
| 36 | (Z)-2-[4-(4-Chloro-1,2-diphenyl-but-1-enyl)-phenylsulfanyl]ethanol |
| 37 | (Z)-2-{4-[4-Chloro-2-(4-chlorophenyl)-1-(4-methoxyphenyl)but-1-enyl]-phenoxy}ethanol |
| 38 | (Z)-1-(2-{4-[4-Chloro-2-(2-chlorophenyl)-1-phenylbut-1-enyl]phenoxy}-ethyl)piperidine |
| 39 | (E)-3-{4-Chloro-1-[4-(2-imidazol-1-yl-ethoxy)phenyl]-2-phenyl-but-1-enyl}-phenol |
| 40 | (Z)-3-{4-Chloro-1-[4-(2-imidazol-1-yl-ethoxy)phenyl]-2-phenyl-but-1-enyl}-phenol |
| 41 | (Z)-2-[4-(4-Chloro-1,2-diphenyl-but-1-enyl)phenylamino]ethanol |
| 42 | (Z)-4-{1-(2-Chloroethyl)-2-[4-(2-hydroxyethoxy)phenyl]-2-phenylvinyl}phenol |
| 43 | (E)-4-{1-(2-Chloroethyl)-2-[4-(2-hydroxyethoxy)phenyl]-2-phenylvinyl}phenol |
| 44 | (Z)-{2-[4-(4-Chloro-1,2-diphenylbut-1-enyl)phenoxy]ethyl}-methylprop-2-ynylamine |
| 45 | (Z)-3-[4-(4-Chloro-1,2-diphenylbut-1-enyl)phenoxymethyl]pentan-3-ol |
| 46 | (Z)-2-[4-(4-Chloro-1,2-diphenylbut-1-enyl)phenoxy]butan-1-ol |
| 47 | N-[4-(4-chloro-1,2-diphenylbut-1-enyl)phenyl]-N',N'-dimethylethane-1,2-diamine |

The structures of the example compounds are summarized as follows:

Compounds with a dimethylaminoethoxy tail

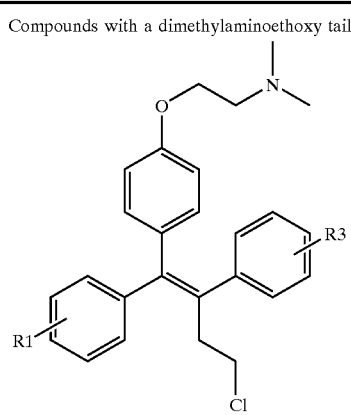

| R1 | R3 | No. |
|---|---|---|
| 4-F | H | 1 and 2 |
| 4-Cl | H | 3 |

-continued

Compounds with a dimethylaminoethoxy tail

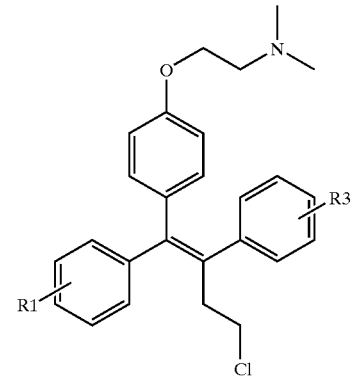

| R1 | R3 | No. |
|---|---|---|
| 4-Cl | 4-Cl | 4 and 5 |
| H | 4-Cl | 23 and 24 |

-continued

Compounds with a dimethylaminoethoxy tail

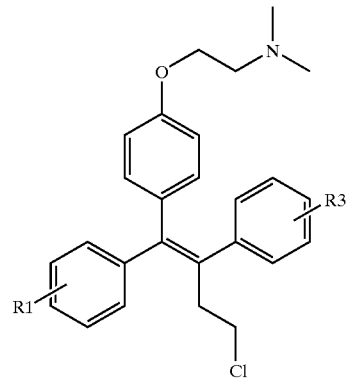

| R1 | R3 | No. |
|---|---|---|
| H | 4-F | 25 |
| 4-OCH$_3$ | 4-Cl | 26 and 27 |

No. 32

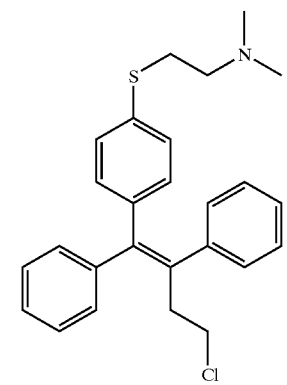

No. 47

-continued

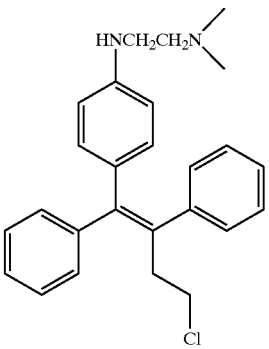

Compounds with a dimethylaminoethoxy tail

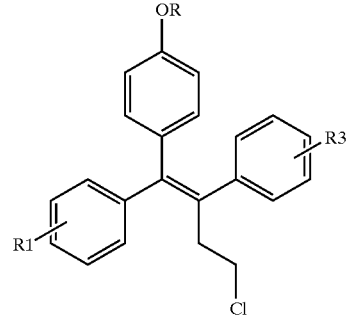

| R1 | R3 | R | No. |
|---|---|---|---|
| H | H | CH$_2$CH$_2$imidazolyl | 21 |
| H | H | CH$_2$CH$_2$N(CH$_3$)CH$_2$CH$_2$OH | 22 |
| H | 3-OCH$_3$ | CH$_2$CH$_2$piperidinyl | 28 and 29 |
| H | 4-OCH$_3$ | CH$_2$CH$_2$piperidinyl | 30 and 31 |
| H | 2-Cl | CH$_2$CH$_2$piperidinyl | 38 |
| 3-OH | H | CH$_2$CH$_2$imidazolyl | 39 and 40 |
| H | H | CH$_2$CH$_2$N(CH$_3$)CH$_2$C≡CH | 44 |

Alcohols

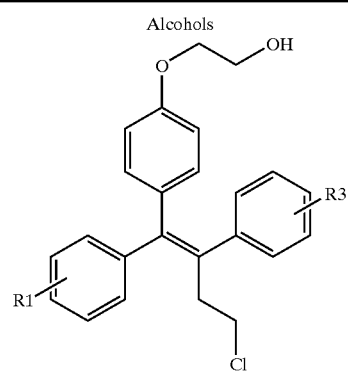

| R1 | R3 | No. |
|---|---|---|
| 4-F | H | 8 |
| 4-Cl | 4-Cl | 9 |
| 4-OCH$_2$CH$_2$OH | H | 16 |
| 4-Cl | H | 17 |

-continued

Alcohols

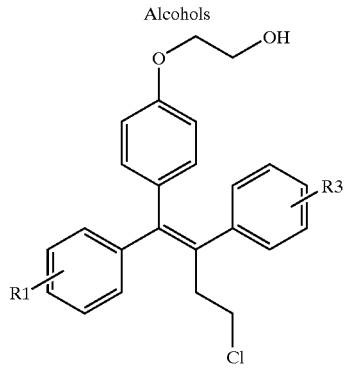

| R1 | R3 | No. |
|---|---|---|
| 3-OH | H | 34 |
| 4-OCH₃ | 4-Cl | 37 |
| H | 4-OH | 42 and 43 |

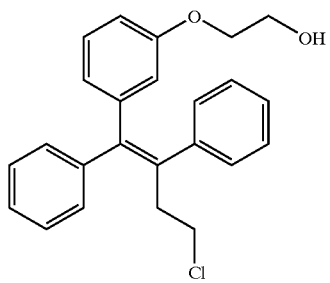
No. 18

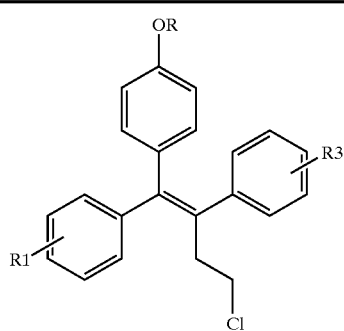

| R1 | R3 | R | No. |
|---|---|---|---|
| 4-Cl | 4-Cl | CH₂CH₂Cl | 6 and 7 |
| 4-Cl | H | CH₂CH(OH)CH₂OH | 10 |
| H | H | CH₂CH₂SCH₃ | 11 |
| 4-Cl | H | CH₂COOH | 12 and 13 |
| 4-Cl | H | CH₂CH₂OCH₂CH₂Cl | 14 |
| 4-F | H | CH₂CH₂OCH₂CH₂Cl | 15 |
| H | H | CH₂CH₂OCH₂CH₂OH | 19 |
| H | H | CH₂CH(OH)CH₂OH | 20 |
| H | H | CH₂CH₂CH₂OH | 35 |
| H | H | CHC(OH)(CH₂CH₃)₂ | 45 |
| H | H | CH(CH₂CH₃)CH₂OH | 46 |

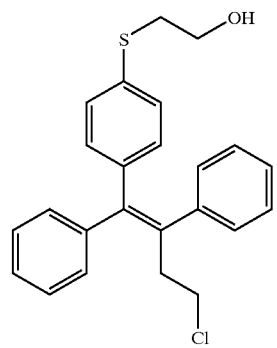
No. 36

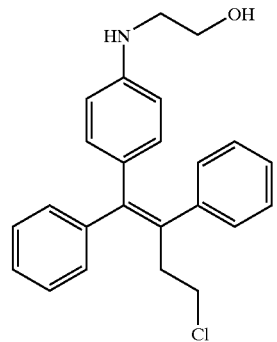
No. 41

The estrogenic and antiestrogenic as well as cytotoxic effects of several compounds in vitro are presented in Table 2. It can be seen that the spectrum of hormonal activity of the compounds varies and thus gives the possibility to use the compounds in different clinical conditions.

Compounds with weak hormonal activity, which kill MCF-7 cells (human breast cancer cells) effectively at the highest investigated concentration (10 $\mu$M) could be used preferably in the treatment of breast cancer. Such compounds are among others compounds No. 1, 3, 16, 19, 26, 27, 39 and 40 (Table 2). These compounds and several others are less effective estrogens and antiestrogens than the well known breast cancer drugs tamoxifen and toremifene (Table 3). Especially compound No. 19 is of interest, because it is a more effective anticancer drug in vivo in the DMBA-induced rat mammary tumor model even at very low doses than clinically used tamoxifen and toremifene (Table 6).

Compounds with weak estrogenic and no antiestrogenic action could be especially suitable for the prevention and treatment of osteoporosis and climacteric symptoms. Such compounds are (among others) compounds No. 3, 10, 11, 18, 19, 20, 25, 32, 36 and 44 (Tables 2, 3 and 4).

Compounds, which decrease cholesterol could be useful as cardiovascular drugs. For women some estrogenicity for such compounds can be allowed, but compounds which are not estrogens or are very weak estrogens and decrease cholesterol, could be used also in men for the prevention and treatment of cardiovascular diseases. Such compounds include (among others) compounds No. 3, 19, 20 (also for men) and 33 (for women) (Table 4). The same compounds are expected to be useful also in the treatment or prevention of Alzheimer's disease. In the latter case the cytotoxic action of the compounds should be weak, like e.g. with compound No. 33 (Table 2). It should be noted that compound No. 19 does not show any estrogenic action on the weight of the prostate gland at doses which are active in DMBA-induced mammary tumor model (Tables 6 and 7). Therefore it could be of special benefit in men and could be of benefit in addition to the above mentioned conditions in the treatment of prostate cancer.

The hormonal profile of the compounds may be in some cases different in vitro and in vivo, e.g. compound No. 1 has no estrogenic action in vitro (Table 2), but is a weak estrogen in vivo (Table 3). Therefore the examples above should be understood as examples of the usefulness in different conditions. They should not be understood as limitations for their possible use in different clinical indications.

TABLE 2

Estrogenic, antiestrogenic, and cytotoxic effects of study compounds in MCF-7 cells. The details of estimations are given in the text. Maximal estrogenic agonism in the absence of estradiol was calculated in per cent of estradiol-stimulus (100%). Antiestrogenic property was evaluated at the concentration of 1 $\mu$mol/l considering theoretical full antagonism as 100 per cent. Toxicity at the concentration of 10 $\mu$mol/l was evaluated as a fraction of dead cells when compared to the control (i.e. 100 means that all cells are dead). Known antiestrogens were used as references.

| Compound No. | Without estradiol (E2) | | With estradiol (E2) | |
|---|---|---|---|---|
| | Maximal Agonism (% of E2) | Maximal Cell Kill (% fraction of dead cells) | Antagonism at 1 $\mu$M (% of full antagonism) | Maximal Cell Kill (% fraction of dead cells) |
| 1 | 1 | 100 | 8 | 100 |
| 2 | 100 | 32 | 29 | 100 |
| 3 | 1 | 100 | 1 | 94 |
| 4 | 10 | 90 | 10 | 100 |
| 5 | 11 | 100 | 31 | 100 |
| 6 | 0 | 47 | 16 | 40 |
| 8 | 31 | 2 | 92 | 52 |
| 9 | 14 | 45 | 9 | 62 |
| 10 | 34 | 7 | 0 | 35 |
| 11 | 14 | 26 | 0 | 55 |
| 14 | 12 | 10 | 27 | 57 |
| 15 | 74 | 82 | 5 | 9 |
| 16 | 22 | 90 | 23 | 96 |
| 17 | 0 | 44 | 17 | 38 |
| 18 | 30 | 10 | 1 | 40 |
| 19 | 14 | 14 | 21 | 50 |
| 20 | 8 | 5 | 25 | 60 |
| 21 | 5 | 80 | 0 | 91 |
| 22 | 1 | 15 | 12 | 41 |
| 23 | 14 | 89 | 5 | 93 |
| 24 | 46 | 89 | 4 | 98 |
| 25 | 17 | 42 | 6 | 27 |
| 26 | 0 | 97 | 11 | 98 |
| 27 | 0 | 99 | 5 | 100 |
| 28 | 3 | 86 | 18 | 92 |
| 30 | 5 | 91 | 4 | 92 |
| 32 | 11 | 86 | 0 | 90 |
| 33 | 20 | 0 | 58 | 80 |
| 34 | 0 | 0 | 0 | 0 |
| 35 | 45 | 50 | 14 | 50 |
| 36 | 8 | 17 | 13 | 37 |
| 37 | 4 | 39 | 0 | 41 |
| 38 | 0 | 99 | 68 | 100 |
| 39 | 0 | 68 | 17 | 78 |
| 40 | 0 | 63 | 3 | 46 |
| 41 | 54 | 0 | 10 | 47 |
| 42 | 9 | 23 | 13 | 54 |
| 43 | 78 | 80 | 6 | 22 |
| 44 | 24 | 78 | 8 | 95 |
| 45 | 15 | 6 | 3 | 19 |
| 46 | 18 | 15 | 23 | 51 |
| Tamoxifen | 31 | 100 | 43 | 100 |
| Toremifene | 37 | 100 | 44 | 100 |
| FC-1271a | 23 | 50 | 21 | 80 |
| ICI 164,384 | 9 | 100 | 100 | 100 |

TABLE 3

Uterotropic (e.g. estrogenic) and estrogen antagonistic effect of study compounds in the 3 day uterotropic assay in immature female rats. Estrogenic effect is estimated as per cent of maximal, estrogen-induced, action. Antiestrogenic effect is presented as per cent of theoretical complete inhibition of estrogen action (100%).

| Compound No. | Uterotropic effect (% of estradiol) Given without estradiol | | Estrogen antagonism (% inhibition of estradiol) Given with estradiol | |
|---|---|---|---|---|
| dose: | 3–5 mg/kg | 10–50 mg/kg | 3–5 mg/kg | 10–50 mg/kg |
| 1 | 42 | 74 | 26 | 31 |
| 3 | 44 | 54 | 65 | 38 |
| 19 | 13 | 37 | 10 | 44 |
| 20 | 33 | 62 | 5 | 20 |
| 20 | 48 | 72 | 26 | 39 |
| 21 | 26 | 39 | 10 | 20 |
| 35 | 43 | 66 | 35 | 32 |
| 36 | 14 | 29 | 0 | 5 |
| 38 | 73 | 72 | 0 | 12 |
| 39 | 9 | 19 | 50 | 70 |
| 40 | 13 | 9 | 45 | 54 |
| 44 | 55 | 75 | n.d. | 42 |
| 45 | 43 | 62 | 30 | 30 |
| 46 | 77 | 100 | 0 | 0 |
| Tamoxifen | 44 | 51 | 51 | 58 |
| Toremifen | 26 | 44 | 45 | 58 |
| Raloxifene | 11 | 13 | 90 | 92 |

Size of the uterus after a 4 weeks treatment of ovariectomized rats with the new compounds (peroral daily doses indicated in mg/kg). Sham-operated, estradiol treated and raloxifene treated ovariectomized rats served as controls.

| Group | | Uterine size (g) |
|---|---|---|
| Sham control | | 0.497 ± 0.103 |
| Ovariectomized | | 0.099 ± 0.016 |
| No. 3 | 3.0 mg/kg | 0.140 ± 0.006 |
| No. 19 | 1.0 mg/kg | 0.192 ± 0.029 |
| No. 19 | 5.0 mg/kg | 0.221 ± 0.023 |
| No. 20 | 1.0 mg/kg | 0.133 ± 0.032 |
| Raloxifene | 3.0 mg/kg | 0.141 ± 0.021 |
| FC-1271a | 5 mg/kg | 0.411 ± 0.042 |

TABLE 4

Effect of compound No. 3, 19 and 20 on rat serum cholesterol level in ovariectomized (OVX) rats after 4 weeks dosing. Estradiol was given to one group for comparison. The result indicates that ovariectomy causes increase of cholesterol level. Estradiol, compound No. 3, 19 and 20 can prevent this increase even at very low dose and decrease the level below the sham operated level. Number of animals was 8 in each group.

| Group | | Cholesterol level (mmol/l) in serum |
|---|---|---|
| Sham operated rat | | 3.8 ± 0.4 |
| OVX rat | | 4.6 ± 0.7 |
| OVX rat + estradiol | 3 μg/kg | 4.0 ± 0.4 |
| OVX + No.3 | 3 mg/kg | 3.1 ± 0.4 |
| OVX + No. 19 | 0.3 mg/kg | 3.6 ± 0.4 |
| OVX + No. 19 | 10 mg/kg | 3.9 ± 0.6 |
| OVX + No. 20 | 1 mg/kg | 3.3 ± 0.6 |
| OVX + No. 20 | 5 mg/kg | 2.3 ± 0.4 |

TABLE 5

Effect of compounds No. 3, 19 and 20 on bone in ovariectomized rats after 4 weeks dosing. Rats were ovariectomized (controls sham operated). Compounds were given for 4 weeks at indicated doses (mg/kg) p.o. beginning one week after the ovariectomy. Tibial epiphyses and femoral neck were prepared for the estimation of the quality of the bone.

| Group and dose (mg/kg) | | | Ash weight (mg) of tibial epiphyses | Maximal load (N) of femoral neck |
|---|---|---|---|---|
| Sham control | | (n = 10) | 34.0 ± 2.9 | 86.7 ± 10.4* |
| OVX | | (n = 10) | 32.2 ± 2.8 | 68.4 ± 8.5 |
| No. 3 | 3.0 mg/kg | (n = 22) | 36.0 ± 3.4* | 92.5 ± 11.1* |
| No. 19 | 1.0 mg/kg | (n = 10) | 34.8 ± 1.3* | 81.6 ± 7.9* |
| No. 19 | 5.0 mg/kg | (n = 10) | 34.9± 1.9* | 85.7 ± 17.0* |
| No. 20 | 3.0 mg/kg | (n = 20) | 35.0 ± 3.2 | 81.7 ± 15.2* |
| Raloxifene | 3.0 mg/kg | (n = 10) | 34.9 ± 3.5 | 84.2 ± 18.4* |

*indicates statistically significant (p < 0.05) difference to ovariectomized animals

TABLE 6

Antitumor effect of compound No. 19 on DMBA-induced rat mammary gland cancer. Compound No. 19 was given p.o. daily for 5 weeks at the indicated doses. Tumors were classified to growing, stable, regressing and disappeared as described in the text. Number of tumors in each group was counted and calculated as per cent of total tumor number. Number of animals in each group was 7. Compound No. 19 did not influence on the body weight of the animals when compared to controls.

| Group | | Growing | Stable | Regressing | Disappeared |
|---|---|---|---|---|---|
| Control | | 82% | 18% | 0% | 0% |
| No. 19 | 3 mg/kg | 20% | 20% | 40% | 20% |
| No. 19 | 15 mg/kg | 14% | 14% | 57% | 14% |
| Tamoxifene | 3 mg/kg | 36% | 56% | 8% | 0% |
| Toremifene | 3 mg/kg | 31% | 51% | 11% | 10% |

TABLE 7

Effect of compound No. 19 on the weight of the prostate gland in intact and castrated male rats after 4 weeks daily treatment with two different doses. Castration decreases markedly the prostate weight and estrogens are known to do the same. Compound No. 19 has no estrogenic effect at the dose of 0.5 mg/kg and is weakly estrogenic at the dose of 5.0 mg/kg. Note that this compound has significant antitumor action in the DMBA-induced mammary cancer model at 0.5 mg/kg dosage (Table 6).

| Group | | Weight of the prostate gland (mg) mean and sd |
|---|---|---|
| Control | | 2.60 ± 0.77 |
| Castrated rats | | 0.59 ± 0.07 |
| No. 19 | 0.5 mg/kg | 2.66 ± 0.21 |
| No. 19 | 5.0 mg/kg | 1.58 ± 0.50 |
| No. 19 | 0.5 mg/kg to castrated rats | 0.59 ± 0.07 |
| No. 19 | 5.0 mg/kg to castrated rats | 0.62 ± 0.07 |

For the purpose of this invention, the novel SERMs, their stereoisomers or pharmaceutically acceptable salts thereof can be administered by various routes. The suitable administration forms include, for example, oral formulations, parenteral injections including intravenous, intramuscular, intradermal and subcutaneous injections; and transdermal or rectal formulations. Suitable oral formulations include e.g. conventional or slow-release tablets and gelatin capsules.

The required dosing of the novel SERMs will vary with the particular condition being treated, the severity of the condition, the duration of the treatment, administration route and specific compounds being employed. Typically the daily dose for an adult person is 5–200 mg, preferably 20–100 mg. SERMs can be given as tablets or other formulations like gelatin capsules alone or mixed in any clinically acceptable non-active ingredients which are used in the pharmaceutical industry.

EXAMPLES

Example 1 a) O-Alkylation of 4-Hydroxybenzophenone Derivatives

In Phase Transfer Catalysis (PTC) Conditions

[4-(2-Dimethylaminoethoxy)phenyl]-(4-fluorophenyl) methanone

4-Hydroxybenzophenone (28.1 g, 0.13 mol) is dissolved in toluene (140 ml). Tetrabutylammonium bromide (TBABr) (2.1 g) is added. Aqueous 48% sodium hydroxide (140 ml) is added at 50–55° C. The mixture is heated to 80° C. and 2-chloroethyldimethylamine hydrochloride (total 20.0 g, 0.14 mol) is added in small portions and the reaction mixture is stirred at 97–100° C. for 3 h. The layers are separated and the organic layer is washed with water, dried over sodium sulfate and evaporated to dryness. Yield 33.0 g, 88%. The product is used for the next step without further purification.

$^1$H NMR (CDCl$_3$): 2.36 (s, 6H), 2.77 (t, 2H), 4.15 (t, 2H), 6.99 (d, 2H), 7.15 (t, 2H), 7.27–7.83 (m, 4H).

Using the same method the following compounds are prepared:

(4-Clorophenyl)-[4-(2-dimethylaminoethoxy)phenyl] methanone $^1$H NMR (CDCl$_3$): 2.36 (s, 6H), 2.77 (t, 2H), 4.15 (t, 2H), 6.98 (d, 2H), 7.45 (2H), 7.71 (d, 2H), 7.79 (d, 2H).

[4-(2-Benzyloxyethoxy)phenyl]-(4-fluorophenyl) methanone $^1$H NMR (CDCl3): 3.87 (dist.t, 2H), 4.24 (dist.t, 2H), 4.65 (s, 2H), 6.99 (d, 2H), 7.15 (t, 2H), 7.32–7.39 (m, 5H), 7.76–7.83 (m, 4H).

[4-(2-Benzyloxyethoxy)phenyl]-(4-chlorophenyl) methanone $^1$H NMR (CDCl$_3$): 3.86 (t, 2H), 4.24 (t, 2H), 4.65 (s, 2H), 6.99 (d, 2H), 7.3–7.4 (m, 5H), 7.45 (d, 2H), 7.70 (d, 2H), 7.78 (d, 2H).

By Acid Catalysis (4-Chlorophenyl)-[4-(tetrahydropyranyloxy)phenyl] methanone

4-Chloro-4'-hydroxybenzophenone (50 g, 0.215 mol) is dissolved in dichloromethane (400 ml). 3,4-Dihydro-2H-pyran (21.7 g, 0.257 mol) and a catalytic amount of p-toluenesulfonic acid are added to the solution. The solution is stirred for 6 hours at room temperature and then allowed to stand over night, 1 N aqueous sodium hydroxide solution (100 ml) is added to the reaction mixture and stirred for 15 minutes. Organic layer is separated and washed twice with 1 N aqueous sodium hydroxide solution and once with water. Dichloromethane solution is dried and evaporated to dryness. Yield 68.6 g.

$^1$H NMR (CDCl$_3$): 1.52–2.20 (m, 6H), 3.60–3.67 (m, 1H), 3.8–3.94 (m, 1H), 5.5–5.6 (m, 1H), 7.10 (d, 2H), 7.45 (d, 2H), 7.72 (d, 2H ), 7.78 (d, 2H).

Using the same method the following compound is prepared:

Bis[4-(tetrahydropyranyloxy)phenyl]methanone $^1$H NMR (CDCl$_3$): 1.55–2.20 (m, 12H), 3.6–3.7 (m, 2H), 3.8–4.0 (m, 2H), 5.5–5.6 (m, 2H), 7.11 (d, 4H), 7.78 (d, 4H).

NaH as a Base (4-Chlorophenyl)-[4-(2,2-dimethyl-[1,3]dioxolan-4-ylmethoxy)-phenyl]-methanone Sodium hydride (3.4 g, 0.072 mol) in oil is washed with heptane and mixed with dimethyl formamide (DMF) (120 ml). 4-Chloro-4'-hydroxybenzophenone (12 g, 0.052 mol) in DMF is added dropwise to the solution and the reaction mixture is stirred for an hour at room temperature. Then toluene-4-sulfonic acid 2,2-dimethyl-[1,3]dioxolan-4-yl methyl ester (17.7 g, 0.0618 mol, prepared from S-1,2-O-iso-propyl glycerol and p-toluenesulfonyl chloride) in DMF is added dropwise to the solution during an hour. The mixture is heated to 60° C. and stirred at that temperature for two days. 1 N aqueous sodium hydroxide solution (200 ml) is added to reaction mixture and the solution is extracted three times with toluene (60 ml). Toluene layers are combined and washed twice with water (60 ml), dried and evaporated to dryness. The residue is crystallized from methanol. Yield 13.7 g, 76.7%.

$^1$H NMR (CDCl$_3$): 1.42 (s, 3H), 1.48 (s, 3H), 3.90–4.24 (m, 4H), 4.52 (quintet, 1H), 6.99 (d, 2H), 7.46 (d, 2H ), 7.71 (d, 2H), 7.79 (d, 2H).

b) Hydroalumination Reaction of Benzophenone Derivatives with Cinnamaldehyde or a Methyl Cinnamate 1-[4-(2-N,N-Dimethylaminoethoxy)phenyl]-1-(4-fluorophenyl)-2-phenylbutane-1,4-diol Lithium aluminum hydride (2.6 g, 0.068 mol) is added into dry tetrahydrofuran (120 ml) under nitrogen atmosphere. Cinnamaldehyde (13.8 g, 0.1 mol) in dry tetrahydrofuran (30 ml) is added at 24–28° C. The reaction mixture is stirred at ambient temperature for 1 h. [4-(2-Dimethylaminoethoxy)phenyl]-(4-fluorophenyl)-methanone (29.6 g, 0.103 mol) in dry tetrahydrofuran (60 ml) is added at 50–55° C. The reaction mixture is stirred at 60° C. for 3 h. Most of tetrahydrofuran is evaporated. Toluene (300 ml), 48% aqueous sodium hydroxide (118 ml) and water (30 ml) are added. The mixture is refluxed for 10 min and the aqueous layer is separated while warm. The NaOH treatment is repeated. The toluene layer is washed twice with hot water. The product is crystallized from toluene as a mixture of stereoisomers (26.4 g, 62%).

$^1$H NMR (CDCl$_3$+MeOH-d$_4$): 1.95–2.12 (m, 2H), 2.30 and 2.37 (2s, together 6H), 2.68 and 2.77 (2t, together 2H), 3.31–3.48 (m, 2H) under which the signal of C$\underline{H}$CH$_2$ of the other diastereoisomer, 3.80 (dd, C$\underline{H}$CH$_2$ the other diastereoisomer), 3.95 and 4.08 (2t, together 2H), 6.62 and 6.91 (2d, together 2H), 7.03 and 6.72 (2t, together 2H), 7.05–7.20 (m, 7H), 7.51 (m, 2H).

Using the same method the following compounds are prepared:

1-(4-Chlorophenyl)-1-[4-(2-N,N-dimethylaminoethoxy) phenyl]-2-phenylbutane 1,4-diol, mixture of stereoisomers.

$^1$H NMR (CDCl$_3$+MeOH-d$_4$): 1.85–2.10 (m, 2H), 2.27 and 2.33 (2s, together 6H), 2.66 and 2.75 (2t, together 2H), 3.25–3.50 (m, 2H), 3.62 and 3.84 (t and dd, together 1H), 3.93 and 4.04 (2t, together 2H), 6.6–7.6 (13H).

1-[4-(2-Benzyloxyethoxy)phenyl]-1-(4-fluorophenyl)-2-phenylbutane-1,4-diol, mixture of stereoisomers.

$^1$H NMR (CDCl$_3$): 1.92–2.15 (m, 2H), 3.30–3.48 and 3.48–3.66 (2m, together 2H), 3.74 and 3.83 (2 dist.t, together 2H), 4.02 and 4.15 (2 dist.t, together 2H), under the two last signal groups C$\underline{H}$CH$_2$, 4.58 and 4.63 (2s, together 2H), 6.6–7.6 (18H).

1-[4-(2-Benzyloxyethoxy)phenyl]-1,2-bis(4-chlorophenyl)butane-1,4-diol, mixture of stereoisomers.

4-Chlorocinnamic acid methyl ester is used instead of cinnamaldehyde.

$^1$H NMR (CDCl$_3$): 1.80–2.15 (m, 2H), 3.2–3.4 and 3.4–3.6 (2m, together 2H), 3.75 and 3.82 (2t, together 2H), 3.95 (dist.t, 1H), 4.00 and 4.14 (2t, together 2H), 4.59 and 4.63 (2s, together 2H), 6.80–7.55 (17H).

1,2-Bis(4-chlorophenyl)-1-[4-(2-dimethylaminoethoxy) phenyl]butane-1,4-diol, mixture of stereoisomers.

4-Chlorocinnamic acid methyl ester is used instead of cinnamaldehyde.

$^1$H NMR (CDCl$_3$+MeOH-d$_4$): 1.85–2.20 (m, 2H), 2.35 and 2.37 (2s, together 6H), 2.77 and 2.82 (2t, together 2H), 3.20–3.45 (m, together 2H), 3.81 and 3.85 (2 dist.t, together 1H), 4.10 and 4.21 (2t, together 2H), 6.9–7.8 (m, 12H).

1,1-Bis[4-(tetrahydropyranyloxy)phenyl]-2-phenylbutane-1,4-diol $^1$H NMR (CDCl$_3$): 1.5–2.1 (m, 14H), 3.3–4.1 (m, 7H), 5.25–5.28 (m, 1H), 6.77 (d, 2H), 7.00 (d, 2H), 7.1–7.2 (m, 9H), 7.47 (d, 2H).

1-(4-Chlorophenyl)-2-phenyl-1-[4-(tetrahydropyranyloxy)phenyl]-butane-1,4-diol $^1$H NMR (CDCl$_3$): 1.5–2.1 (m, 8H), 3.2–4.0 (m, 5H), 5.27 (m, 1H), 6.79 (d, 2H), 6.9–7.32 (m, 9H), 7.5 (d, 2H).

1-(4-Chlorophenyl)-[4-(2,2-dimethyl-[1,3]dioxotan-4-ylmethoxy)-phenyl]-2-phenylbutane-1,4-diol $^1$H NMR (CDCl$_3$): 1.37 and 1.40 and 1.42 and 1.46 (4s, together 6H), 1.9–2.1 (m, 2H), 3.2–4.5 (m, 8H), 6.6–7.55 (m, 13H).

1,2-Diphenyl-1-[3-(tetrahydropyranyloxy)phenyl]-butane-1,4-diol is prepared starting from phenyl-[3-(tetrahydropyranyloxy) phenyl]methanone and cinnamaldehyde. The compound is used in the next reaction step without further purification.

c) Dehydration of 1,1,2-triarylbutane-1,4-diol Derivatives

4-[4-(2-Dimethylaminoethoxy)phenyl]-4-(4-fluorophenyl)-3-phenylbut-3-en-1-ol

1-[4-(2-N,N-Dimethylaminoethoxy)phenyl]-1-(4-fluorophenyl)-2-phenylbutane-1,4-diol (8.46 g. 0.02 mol) is refluxed in 80 ml of acetic anhydride for 3 h. The mixture is cooled to 60° C. and acetyl chloride (7.85 g, 0.1 mol) is added. The mixture is stirred at 80–90° C. for 4 h. The solvents are evaporated. Solution containing 5% of sodium hydroxide in 80% aqueous methanol is added and the mixture is stirred for 2 h at RT. Methanol is evaporated. Water is added and the product is extracted into ethyl acetate. The organic layer is washed with water, dried and evaporated. The residue (9.5 g) is mixture of E- and Z-isomers of the product. The isomers are separated by flash chromatography (eluent: toluene:triethylamine 9:1).

E-isomer, $^1$H NMR (CDCl$_3$): 2.27 (s, 6H), 2.64 (t, 2H), 2.74 (t, 2H), 3.57 (t, 2H), 3.92 (t, 2H), 6.57 (d, 2H), 6.75 (d, 2H), 7.03 (t, 2H), 7.10–7.18 (m, 5H), 7.27 (dd, 2H).

Z-isomer, $^1$H NMR (CDCl$_3$): 2.34 (s, 6H), 2.74 (t, 2H), 2,79 (t, 2H), 3.60 (t, 2H), 4.05 (t, 2H), 6.69 (t, 2H), 6.84 (dd, 2H), 6.91 (d, 2H), 7.09–7.17 (m, 5H), 7.20 (d, 2H).

Using the same method the following compounds are prepared:

4-(4-Chlorophenyl)-4-[4-(2-dimethylaminoethoxy) phenyl]-3-phenylbut-3-en-1-ol

E-isomer, $^1$H NMR (CDCl$_3$): 2.27 (s, 6H), 2.64 (t, 2H), 2.73 (t, 2H), 3.56 (t, 2H), 3.91 (t, 2H), 6.56 (d, 2H), 6.74 (d, 2H), 7.10–7.34 (m, 9H).

4-[4-(2-Benzyloxyethoxy)phenyl]-4-(4-fluorophenyl)-3-phenylbut-3-en-1-ol

E-isomer, $^1$H NMR (CDCl$_3$): 2.74 (t, 2H), 3.57 (m, 2H), 3.74 (dist.t, 2H), 4.01 (dist.t, 2H), 4.58 (s, 2H), 6.57 (d, 2H), 6.75 (d, 2H), 7.00–7.40 (m, 14H) from which the signal 7.03 (t, 2H) can be identified.

Z-isomer, $^1$H NMR (CDCl$_3$): 2.79 (t, 2H), 3.60 (m, 2H), 3.84 (dist.t, 2H), 4.17 (dist.t, 2H), 4.65 (s, 2H), 6.69 (t, 2H), 6.83 (dd, 2H), 6.91 (d, 2H), 7.00–7.45 (m, 14H) from which the signal 7.20 (d, 2H) can be identified.

4-[4-(2-Benzyloxyethoxy)phenyl]-3,4-bis(4'-chlorophenyl)-but-3-en-1-ol

E-isomer, $^1$H NMR (CDCl$_3$): 2.70 (t, 2H), 3.50–3.65 (m, 2H), 3.75 (dist.t, 2H), 4.03 (dist.t, 2H), 4.59 (s, 2H), 6.59 (d, 2H), 6.73 (d, 2H), 7.00–7.40 (m, 13H).

3,4-Bis(4-chlorophenyl)-4-[4-(2-hydroxyethoxy)pheny]but-3-en-1-ol is produced as a sideproduct in the dehydration reaction of 1-[4-(2-benzyloxyethoxy)phenyl]-1,2-bis(4-chlorophenyl)butane-1,4-diol.

E-isomer, $^1$H NMR (CDCl$_3$): 2.72 (t, 2H), 3.50–3.65 (m, 2H), 3.80–3.96 (m, 4H), 6.59 (d, 2H), 6.75 (d, 2H), 7.00–7.40 (m, 8H).

Z-isomer, $^1$H NMR (CDCl$_3$+MeOH-d$_4$): 2.75 (t, 2H), 3.56 (t, 2H), 3.95 (t, 2H), 4.09 (t, 2H), 6.79 (d, 2H), 6.91 (d, 2H), 7.01 (d, 2H), 7.05 (d, 2H), 7.16 (d, 2H), 7.19 (d, 2H).

3,4-Bis(4-Chlorophenyl)-4-[4-(2-dimethylaminoethoxy)phenyl]but-3-en-1-ol

E-isomer, $^1$H NMR (CDCl$_3$): 2.29 (s, 6H), 2.66 (t, 2H), 2.72 (t, 2H), 3.57 (t, 2H), 3.94 (t, 2H), 6.60 (d, 2H), 6.73 (d, 2H), 7.06 (d, 2H), 7.15 (d, 2H), 7.23 (d, 2H), 7.32 (d, 2H).

Z-isomer, HCl-salt, $^1$H NMR (MeOH-d$_4$):), 2.77 (t, 2H), 3.03 (s, 6H ), 3.53 (t, 2H), 3.65 (t, 2H), 4.42 (t, 2H), 6.89 (d, 2H), 7.08 (d, 2H), 7.10 (d, 2H), 7.16 (d, 2H), 7.23 (d, 2H), 7.31 (d, 2H).

4,4-Bis(4-hydroxyphenyl)-3-phenylbut-3-en-1-ol

The protecting tetrahydropyranyl (THP) groups are removed in the dehydration reaction.

$^1$H NMR (CDCl$_3$): 2.76 (t, 2H), 3.54 (m, 2H), 6.46 (d, 2H), 6.70 (d, 2H), 6.80 (d, 2H), 7.0–7.2 (m, 7H).

4-(4-Chlorophenyl)-4-(4-hydroxyphenyl)-3-phenylbut-3-en-1-ol

The protecting THP-group is removed in the dehydration reaction.

E-isomer $^1$H NMR (CDCl$_3$): 2.65 (t, 2H), 3.45 (t, 2H), 6.29 (d, 2H), 6.49 (d, 2H), 7.00–7.15 (m, 5H), 7.24 (d, 2H), 7.33 (d, 2H).

Z-isomer $^1$H NMR (CDCl$_3$): 2.79 (t, 2H), 3.58 (t, 2H), 6.80 (d, 2H), 6.81 (d, 2H), 6.97 (d, 2H), 7.1–7.2 (m, 7H).

4-(4-Chlorophenyl)-4-[4-(2,3-dihydroxypropyloxy)phenyl]-3-phenylbut-3-en-1-ol

The 2,2-dimethyl-[1,3]dioxolan ring is cleaved in the reaction.

E-isomer $^1$H NMR (CDCl$_3$): 2.73 (t, 2H), 3.55 (t, 2H), 3.60–3.77 (m, 2H), 3.87–4.05 (m, 3H), 6.56 (d, 2H), 6.76 (d, 2H), 7.1–7.35 (m, 9H).

3-(4-Hydroxy-1,2-diphenylbut-1-enyl)phenol

The protecting THP-group is removed in the dehydration reaction.

Z-isomer $^1$H NMR (CDCl$_3$): 2.73 (t, 2H), 3.55 (t, 2H), 6.4–7.4 (m, 12H).

d) Conversion of the Hydroxy Group of 3,3,4-triarylbut-3-en-1-ols to Chlorine
By Thionyl Chloride (E)-(2-{4-[4-Chloro-1-(4-fluorophenyl)-2-phenylbut-1-enyl]phenoxy}ethyldimethylamine (No.1)

(E)-4-[4-(2-Dimethylaminoethoxy)phenyl]-4-(4-fluorophenyl)-3-phenylbut-3-en-1-ol (0.8 g, 2 mmol) is dissolved in toluene (30 ml) and thionyl chloride (0.7 g, 6 mmol) is added. The mixture is refluxed for an hour. Toluene is partly evaporated. The crystallized hydrochloride salt of the product is filtered off and the precipitate is washed with toluene. The yield is 0.79 g, 86%.

$^1$H NMR (HCl salt, MeOH-d$_4$): 2.90 (t, 2H), 2.92 (s, 6H), 3.40 (t, 2H), 3.49 (dist.t, 2H), 4.21 (dist.t, 2H), 6.70 (d, 2H), 6.85 (d, 2H), 7.11 (t, 2H), 7.12–7.22 (m, 5H), 7.32 (dd, 2H).

Using the same method the following compounds are prepared:

(Z)-(2-{4-[4-Chloro-1-(4-fluorophenyl)-2-phenylbut-1-enyl]phenoxy}ethyldimethylamine (No. 2)

$^1$H NMR (HCl salt, MeOH-d$_4$): 2.93 (t, 2H), 2.99 (s, 6H), 3.42 (t, 2H), 3.61 (dist.t, 2H), 4.39 (dist.t, 2H), 6.73 (t, 2H), 6.88 (dd, 2H), 7.07 (d, 2H), 7.12–7.22 (m, 5H), 7.29 (d, 2H).

(E)-(2-{4-[4-Chloro-1-(4-chlorophenyl)-2-phenylbut-1-enyl]phenoxy}-ethyl)dimethylamine (No. 3)

$^1$H NMR (CDCl$_3$): 2.30 (s, 6H), 2.66 (t, 2H), 2.91 (t, 2H1), 3.40 (t, 2H), 3.94 (t, 2H), 6.57 (d, 2H), 6.75 (d, 2H), 7.1–7.4 (m, 9H).

(2-{4-[4-Chloro-1,2-bis(4-chlorophenyl)but-1-enyl]phenoxy}ethyl)dimethylamine (No. 4 and 5)

E-isomer (No. 4). HCl-salt, $^1$H NMR (CDCl$_3$): 2.90 (s, 6H), 2.94 (t, 2H), 3.40 (t, 4H), 4.38 (t, 2H), 6.59 (d, 2H), 6.78 (d, 2H), 7.06 (d, 2H), 7.19 (d, 2H), 7.23 (d, 2H), 7.35 (d, 2H).

Z-isomer (No. 5), HCl-salt, $^1$H NMR (MeOH-d$_4$):), 2.95 (t, 2H), 3.41 (s, 6H ), 3.41 (t, 2H), 3.48–3.58 (m, 2H), 4.56–4.65 (m, 2H), 6.79 (d, 2H), 6.92 (d, 2H), 7.02 (d, 2H), 7.05 (d, 2H), 7.19 (d, 2H), 7.22 (d, 2H).

(E)-1-[4-(2-Benzyloxyethoxy)pheny]-4-chloro-1-(4-fluorophenyl)-2-phenylbut-1-ene $^1$H NMR (CDCl$_3$): 2.92 (t, 2H), 3.41 (t, 2H), 3.74 (dist.t, 2H), 4.01 (dist.t, 2H), 4.59 (s, 2H), 6.58 (d, 2H), 6.76 (d, 2H), 7.06 (t, 2H), 7.10–7.40 (m, 12H).

(E)-1-[4-(2-Benzyloxyethoxy)phenyl]-4-chloro-1,2-bis(4-chlorophenyl)-but-1-ene $^1$H NMR (CDCl$_3$): 2.90 (t, 2H), 3.39 (t, 2H), 3.76 (dist.t, 2H), 4.04 (dist.t, 2H), 4.60 (s, 2H), 6.60 (d, 2H), 6.74 (d, 2H), 7.06 (d, 2H), 7.17 (d, 2H), 7.23 (d, 2H), 7.25–7.4 (m, 7H).

4-Chloro-1-[4-(2-chloroethoxy)phenyl]-1,2-bis(4-chlorophenyl)-but-1-ene (No. 6 and 7)

is prepared from 3,4-bis(4-chlorophenyl)-4-[4-(2-hydroxyethoxy)phenyl]but-3-en-1-ol.

E-isomer (No.6), $^1$H NMR (CDCl$_3$): 2.90 (t, 2H), 3.39 (m, 2H), 3.73 (t, 2H), 4.10 (t, 2H), 6.59 (d, 2H), 6.76 (d, 2H), 7.10 (d, 2H), 7.17 (d, 2H), 7.23 (d, 2H), 7.33 (d, 2H).

Z-isomer (No. 7), ¹H NMR (CDCl₃): 2.94 (t, 2H), 3.40 (t, 2H), 3.83 (t, 2H), 4.25 (t, 2H), 6.79 (d, 2H), 6.92 (d, 2H), 7.02 (d, 2H), 7.05 (d, 2H), 7.18 (d, 2H), 7.20 (d, 2H).

By Triphenylphosphine-carbon Tetrachloride 1-(2,2-Dimethyl-[1,3]dioxolan-4-ylmethoxy)phenyl-4-chloro-1-(4-chlorophenyl)-2-phenyl-but-1-ene Triphenyl phosphine (0.19 g, 0.73 mmol) is dissolved in acetonitrile (4 ml). Carbon tetrachloride (0.237 g, 1.3 mmol) and triethylamine (0.043 g, 0.43 mmol) is added to the solution and the mixture is stirred for half an hour at ambient temperature. 4-(2,2-Dimethyl-[1,3]dioxolan-4-ylmethoxy)phenyl-4-(4-chloroplhenyl)-3-phenylbut-3-en-1-ol (0.2 g, 0.43 mmol, prepared from 4-(4-chlorophenyl)-4-[4-(2,3-dihydroxypropyloxy)phenyl]-3-phenylbut-3-n-1-ol by protecting the diol group as acetonide) is dissolved in acetonitrile, added to the reaction mixture and stirring is continued for additional 2 hours. Then the solvent is evaporated and the residue is dissolved in 20 ml of methanol-water-solution (8:2). Solution is extracted twice with petroleum ether (20 ml) at boiling point. Petroleum ether phases are combined and washed once again with hot methanol-water solution. Yield 0.07 g.

E-isomer ¹H NMR (CDCl₃): 1.37 and 1.41 (2s, together 6H), 2.91 (t, 2H), 3.40 (t, 2H), 3.70–4.14 (m, 4H), 4.39 (quintet, 1H), 6.56 (d, 2H), 6.76 (d, 2H), 7.05–7.4 (m, 9H).

e) Removal of the Protecting Groups (E)-2-{4-[4-Chloro-2-phenyl-1-(4-fluorophenyl)but-1-enyl]phenoxy}ethanol (No. 8)

(E)-1-[4-(2-Benzyloxyethoxy)phenyl]-4-chloro-1-(4-fluorophenyl)-2-phenylbut-1-ene (400 mg, 0.8 mmol) is dissolved in toluene. Zn (106 mg, 1.6 mmol) and acetyl chloride (126 mg, 1.6 mmol) are added under nitrogen atmosphere. The mixture is stirred at room temperature for 6 h. The mixture is filtered and the solvent evaporated. The residue is dissolved in 80% aqueous methanol containing 5% of sodium hydroxide. The mixture is stirred at room temperature for 2 h and methanol is evaporated. Some water is added and the product is extracted into ethyl acetate. The mixture is dried and the solvent is evaporated. The product is purified by flash chromatography (eluent toluene:methanol 9:1).

¹H NMR (CDCl₃): 2.92 (t, 2H, ), 3.41 (t, 2H), 3.87–3.95 (m, 4H), 6.57 (d, 2H), 6.78 (d, 2H), 7.06 (t, 2H), 7.10–7.31 (m, 7H).

Using the same method the following compound included in the invention is prepared:

(E)-2-{4-[(Z)-4-Chloro-1,2-bis(4-chlorophenyl)but-1-enyl]phenoxyl}ethanol (No. 9)

¹H NMR (CDCl₃): 2.90 (t, 2H), 3.39 (t, 2H), 3.85–4.05 (m, 4H). 6.61 (d, 2H), 6.77 (d, 2H), 7.07 (d, 2H), 7.1–7.26 (m, 4H), 7.35 (d, 2H).

(E)-3-{4-[(Z)-4-Chloro-1-(4-chlorophenyl)-2-phenyl-but-1-enyl]phenoxy}propane-1,2-diol (No. 10)

1-(2,2-Dimethyl-[1,3]dioxolan-4-ylmethoxy)phenyl-4-chloro-1-(4-chlorophenyl)-2-phenyl-but-1-ene (0.5 g, 1.0 mmol) is dissolved in ethanol and 2 N aqueous hydrogen chloride (5 ml) is added to the solution. The mixture is heated to 40° C. and stirring is continued for an hour. Then ethanol is evaporated and the product is extracted in toluene, which is washed with water, dried and evaporated to drness. Yield 0.45 g.

¹H NMR (CDCl₃): 2.91 (t, 2H), 3.41 (t, 2H), 3.60–4.15 (m, 5H), 6.56 (d, 2H), 6.77 (d, 2H), 7.1–7.4 (m, 9H).

Example 2 a) O-Alkylation of 4-(1,2-diaryl-4-hydroxybut-1-enyl)phenol Derivatives 4,4-Bis[4-(2-benzyloxyethoxy)phenyl]-3-phenyl but-3-en-1-ol is prepared from 4,4-bis(4-hydroxyphenyl)-3-phenylbut-3-en-1-ol (example 1c) and benzyl 2-bromoethyl ether by PTC reaction according to the method described in the example 1 a.

¹H NMR (CDCl₃): 2.78 (t, 2H), 3.59 (q, 2H), 3.74, 3.84, 4.02 and 4.17 (4 dist.t, together 8H), 4.59 (s, 2H), 4.65 (s, 2H), 6.56 (d, 2H), 6.76 (d, 2H), 6.91 (d, 2H), 7.09–7.40 (m, 17H).

Using the same method the following compounds are prepared:

(E)-4-[4-(2-Benzyloxyethoxy)phenyl]-4-(4-chlorophenyl)-3-phenyl-but-3-en-1-ol

¹H NMR (CDCl₃): 2.74 (t, 2H), 3.56 (t, 2H), 3.71–3.76 (m, 2H), 3.98–4.03 (m, 2H), 4.60 (s, 2H), 6.57 (d, 2H), 6.75 (d, 2H), 7.10–7.40 (m, 14H).

(Z)-4-[3-(2-Benzyloxyethoxy)phenyl]-3,4-diphenyl-but-3-en-1-ol

¹H NMR (CDCl₃): 2.75 (t, 2H), 3.58 (t, 2H), 3.63–3.66 (m, 2H), 3.81–3.85 (m, 2H), 4.55 (s, 2H), 6.47–7.40 (m, 19H).

(Z)-4-[4-(2-Methylsulfanylethoxy)phenyl]-3 4-diphenyl-but-3-en-1-ol

The compound is prepared by using the method described in the example 1a starting from 4-(4-hydroxyphenyl)-3,4-diphenyl-but-3-en-1-ol (preparation described in U.S. Pat. No. 4,996,225) and 2-chloroethyl methyl sulfide.

¹H NMR (CDCl₃): 2.16 (s, 3H), 2.75 (t, 2H), 2.79 (t, 2H), 3.59 (q, 2H), 4.02 (t, 2H), 6.55 (d, 2H), 6.79 (d, 2H), 7.05–7.40 (m, 10H).

(Z)-4-[4-(3-Benzyloxypropoxy)phenyl]-3,4-diphenyl-but-3-en-1-ol is prepared by the same method using benzyl 3-bromopropyl ether as a reagent.

¹H NMR (CDCl₃): 2.00 (quint., 2H), 2.75 (t, 2H), 3.59 (2×t, 4H), 3.95 (t, 2H), 4.48 (s, 2H), 6.54 (d, 2H), 6.78 (d, 2H), 7.11–7.40 (m, 15H).

(E)-4-(4-Chlorophenyl)-3-phenyl-4-(4-{2-[2-(tetrahydropyranyloxy)ethoxy]-ethoxy}phenyl)but-3-en-1-ol NaH (0.09 g, 2.69 mmol) is mixed with dimethylformamide (DMF) (30 ml). (E)-4-(4-Chlorophenyl)-4-(4-hydroxyphenyl)-3-phenylbut-3-en-1-ol is dissolved in the solution and the mixture is heated to 60° C. and stirred for half an hour. 2-[(2-(Tetrahydropyranyloxy)ethoxy]ethyl chloride (0.83 g, 4.03 mmol) dissolved in DMF (5 ml) is added to the solution and heating is continued for 3 hours. Saturated aqueous ammonium chloride solution (30 ml) and toluene (30 ml) is added to the cooled reaction mixture and stirring is continued for 10 minutes. Layers are separated and aqueous layer is extracted with toluene (30 ml). Toluene phases are combined and washed with 2 N aqueous sodium hydroxide and three times with water. Organic phase is dried and evaporated to dryness. Yield 1.4 g, 99%.

¹H NMR (CDCl₃): 1.40–1.90 (m, 6H), 2.70 (t, 2H), 3.4–3.94 (m, 10H), 3.95–4.05 (m, 2H), 4.55 (m, 1H), 6.56 (d, 2H), 6.74 (d, 2H), 7.05–7.35 (m, 9H).

Using the same method the following compounds are prepared:

(Z)-3,4-Diphenyl-4-(4-{2-[(2-(tetrahydropyranyloxy)ethoxyl]-ethoxy}phenyl)but-3-en-1-ol is prepared by the same method as previous compound starting from 4-(4-hydroxyphenyl)-3,4-diphenyl-but-3-en- 1-ol (preparation described in U.S. Pat. No. 4,996,225) and 2-[2-(tetrahydropyranyloxy)ethoxy]ethyl chloride $^1$H NMR (CDCl$_3$): 1.40–1.91 (m, 6H), 2.74 (t, 2H), 3.4–4.0 (m. 12H), 4.61 (m, 1H), 6.55 (d, 2H), 6.77 (d, 2H), 7.05–7.35 (m, 10H).

4-(4-Fluoropheny)-3-pheny-4-(4-{2-[2-(tetrahydropyranyloxy)ethoxy]-ethoxy}phenyl)but-3-en-1-ol E-isomer $^1$H NMR (CDCl$_3$): 1.38–1.90 (m, 6H), 2.75 (t, 2H), 3.32–4.03 (m, 10H), 4.00 (m, 2H), 4.62 (m, 1H), 6.56 (d, 2H), 6.75 (d, 2H), 7.04 (t, 2H), 7.0–7.20 (m, 5H), 7.27 (dd, 2H).

Z-isomer $^1$H NMR (CDCl$_3$): 1.40–1.90 (m, 6H), 2.79 (t, 2H), 3.43–4.03 (m, 10H), 4.15 (m, 2H), 4.65 (m, 1H), 6.69 (t, 2H), 6.83 (dd, 2H), 6.90 (d, 2H), 7.05–7.20 (m, 5H), 7.19 (d, 2H).

(Z)-4-[4-(2,2-Dimethyl-[1,3]-dioxolan-4-ylmethoxy)phenytl-3,4-diphenylbut-3-en-1-ol $^1$H NMR (CDC$_3$): 1.37 and 1.41 (2s, together 6H), 2.75 (t, 2H), 3.58 (t, 2H), 3.70–4.10 (m, 4H), 4.39 (quintet, 1H), 6.56 (d, 2H), 6.78 (d, 2H), 7.10–7.40 (m, 10H).

{4-[1-(4-Chlorophenyl)-4-hydroxy-2-phenylbut-1-enyl] phenoxy}acetic acid ethyl ester is prepared from 4-(4-chlorophenyl)-4-(4-hydroxyphenyl)-3-phenylbut-3-en-1-ol (example 1c.) and ethyl bromoacetate according to the procedure described in the example 1a using NaH as a base.

E-isomer $^1$H NMR (CDCl$_3$): 1.25 (t, 3H), 2.74 (t, 2H), 3.57 (t, 2H), 4.22 (q, 2H), 4.48 (s, 2H), 6.56 (d, 2H), 6.77 (d, 2H), 7.0–7.4 (m, 9H).

Z-isomer $^1$H NMR (CDCl$_3$): 1.31 (t, 3H), 2.78 (t, 2H), 3.58 (t, 2H), 4.29 (q, 2H), 4.63 (s, 2H), 6.79 (d, 2H), 6.89 (d, 2H), 6.98 (d, 2H), 7.15–7.30 (m, 7H).

b) Conversion of the Hydroxyl Group to Chlorine 1,1-Bis[4-(2-benzyloxyethoxy)phenyl]-4-chloro-2-phenyl-but-1-ene Conversion of the hydroxy group to chlorine is carried out using thionyl chloride as a reagent according to the procedure described in the example 1d.

$^1$H NMR (CDCl$_3$): 2.94 (t, 2H), 3.42 (t, 2H), 3.73 and 3.83 (2 dist.t., together 4H), 4.00 and 4.16 (2 dist.t., together 4H), 4.58 (s, 2H), 4.65 (s, 2H), 6.56 (d, 2H), 6.76 (d, 2H), 6.92 (d, 2H), 7.10–7.40 (m, 17H).

Using the same method the following compounds are prepared:

(E)-1-[4-(2-Benzyloxyethoxy)phenyl]-4-chloro-1-(4-chlorophenyl)-2-phenyl-but-1-ene $^1$H NMR (CDCl$_3$): 2.91 (t, 2H), 3.40 (t, 2H), 3.71–3.76 (m, 2H), 3.98–4.03 (m, 2H), 4.60 (s, 2H), 6.57 (d, 2H), 6.75 (d, 2H), 7.10–7.40 (m, 14H).

(Z)-4-Chloro-1-[4-(2-methylsulfanylethoxy)phenyl]-1,2-diphenyl-but-1-ene (No. 11)

$^1$H NMR (CDCl$_3$): 2.16 (s, 3H), 2.79 (t, 2H), 2.92 (t, 2H), 3.42 (t, 2H), 4.01 (t, 2H), 6.55 (d, 2H), 6.78 (d, 2H), 7.05–7.45 (m, 10H).

(Z)-1-[3-(2-Benzyloxyethoxy)phenyl]-4-chloro-1,2-diphenyl-but-1-ene $^1$H NMR (CDCl$_3$): 2.92 (t, 2H), 3.41 (t, 2H), 3.63–3.67 (m, 2H), 3.81–3.85 (m, 2H), 4.55 (s, 2H), 6.47–7.40 (m, 19H).

(Z)-1-[4-(3-Benzyloxypropoxy)phenyl]-4-chloro-1,2-diphenyl-but-1-ene $^1$H NMR (CDCl$_3$): 2.0 (quintet, 2H), 2.92 (t, 2H), 3.42 (t, 2H), 3.59 (t, 2H), 3.94 (t, 2H), 4.48 (s, 2H), 6.54 (d, 2H), 6.78 (d, 2H), 7.11–7.40 (m, 15H).

{4-[4-Chloro-1-(4-chlorophenyl)-2-phenylbut-1-enyl] phenoxy}acetic acid ethyl ester and the corresponding acid (No. 12 and 13)

E-isomer, ethyl ester $^1$H NMR (CDCl$_3$): 1.25 (t, 3H), 2.91 (t, 2H), 3.41 (t, 2H), 4.21 (q, 2H), 4.49 (s, 2H), 6.57 (d, 2H), 6.77 (d, 2H), 7.0–7.4 (m, 9H).

The ester is hydrolyzed to the corresponding acid in 80% aqueous methanol containing 5% of sodium hydroxide.

E-isomer, acid (No. 12) $^1$H NMR (CDCl$_3$): 2.91 (t, 2H), 3.41 (t, 2H), 4.47 (s, 2H), 6.58 (d, 2H), 6.78 (d, 2H), 7.0–7.4 (m, 9H).

Z-isomer, ethyl ester $^1$H NMR (CDCl$_3$): 1.31 (t, 3H), 2.95 (t, 2H), 3.42 (t, 2H). 4.30 (q, 2H), 4.65 (s, 2H), 6.79 (d, 2H), 6.91 (d, 2H), 6.98 (d, 2H), 7.15–7.30 (m, 7H).

Z-isomer, acid (No. 13) $^1$H NMR (CDCl$_3$): 2.95 (t, 2H), 3.41 (t, 2H), 4.65 (s, 2H), 6.79 (d, 2H), 6.94 (d, 2H), 6.98 (d, 2H), 7.10–7.30 (m, 7H).

(Z)-1,2-Diphenyl-4-chloro-4-(4-{2-[2-(tetrahydropyranyloxy)ethoxyl]-ethoxy}phenyl)-but-1-ene Conversion of hydroxy group to chlorine is carried out using Ph3P and CCl$_4$ as reagents according to the procedure described in the example 1d.

$^1$H NMR (CDCl$_3$): 1.30–1.90 (m, 6H), 2.92 (t, 2H), 3.42 (t, 2H), 3.4–4.0 (m, 10H), 4.62–4.65 (m, 1H), 6.55 (d, 2H), 6.77 (d, 2H), 7.05–7.35 (m, 10H).

Using the same method the following compounds are prepared:

(Z)-4-[4-(4-Chloro-1,2-diphenyl-but-1-enyl) phenoxymethyl]-2,2-dimethyl-[1,3]dioxolane $^1$H NMR (CDCl$_3$): 1.37 and 1.41 (2s, together 6H), 2.91 (t, 2H), 3.41 (t, 2H), 3.7–4.1 (m, 4H), 4.39 (quintet, 1H), 6.55 (d, 2H), 6.77 (d, 2H), 7.10–7.41 (m, 10H).

(E)-1-(4-{2-[(2-Chloroethoxy]ethoxy}phenyl)-4-chloro-1-(4-chlorophenyl)-2-phenyl-but-1-ene (No. 14)

The tetrahydropyranyloxy group is also converted to chlorine in the reaction.

$^1$H NMR (CDCl$_3$): 2.94 (t, 2H), 3.43 (t, 2H), 3.65 (dist.t, 2H), 3.8–3.85 (m, 4H), 4.0–4.06 (m, 2H), 6.60 (d, 2H), 6.78 (d, 2H), 7.10–7.40 (m, 9H).

(E)-1-(4-{2-[(2-Chloroethoxylethoxy]phenyl)-4-chloro-1-(4-fluorophenyl)-2-phenyl-but-1-ene (No. 15)

The tetrahydropyranyloxy group is also converted to chlorine in the reaction.

$^1$H NMR (CDCl$_3$): 2.91 (t, 2H), 3.41 (t, 2H), 3.62 (dist.t, 2H), 3.74–3.85 (m, 4H), 4.01 (dist.t, 2H ), 6.57 (d, 2H), 6.76 (d, 2H), 7.06 (t, 2H), 7.09–7.22 (m, 5H), 7.27 (dd, 2H).

c) Removal of the Protecting Groups 2-(4-{4-Chloro-1-[4-(2-hydroxyethoxy)phenyl]-2-phenyl-but-1-enyl}-phenoxy)-1-ethanol (No. 16)

The benzyl groups are removed using Zn and AcCl as reagents according to the method described in the example 1e.

$^1$H NMR (CDCl$_3$): 2.95 (t, 2H), 3.42 (t, 2H), 3.80–4.20 (m, 8H), 6.56 (d, 2H), 6.78 (d, 2H), 6.92 (d, 2H), 7.10–7.26 (m, 7H).

Using the same method the following compounds included in the invention are prepared:

(E)-2-{4-[4-Chloro-2-phenyl-1-(4-chlorophenyl)but-1-enyl]phenoxy}ethanol (No. 17)

$^1$H NMR (CDCl$_3$): 2.92 (t, 2H), 3.41 (t, 2H), 3.80–4.00 (m, 4H), 6.57 (d, 2H), 6.77 (d, 2H), 7.10–7.40 (m, 9H).

(Z)-2-[3-(4-Chloro-1,2-diphenyl-but-1-enyl)phenoxy] ethanol (No. 18)

$^1$H NMR (CDCl$_3$): 2.93 (t, 2H), 3.41 (t, 2H), 3.70–3.80 (m, 4H), 6.40–7.40 (m,14 H).

(Z)-2-{2-[4-(4-Chloro-1,2-diphenylbut-1-enyl)phenoxy] ethoxy}ethanol (No. 19)

The tetrahydropyranyl ether is cleaved with H$^+$/EtOH using the method described in the example 1e.

$^1$H NMR (CDCl$_3$): 2.92 (t, 2H), 3.41 (t, 2H), 3.61, 3.68, 3.77 (3 dist.t, 6H), 4.00 (dist.t, 2H), 6.56 (d, 2H), 6.78 (d, 2H), 7.1–7.4 (m, 10H).

Using the same method the following compound included in the invention is prepared:

(Z)-3-[4-(4-Chloro-1,2-diphenyl-but-1-enyl)phenoxy] propane-1,2-diol (No. 20)

$^1$H NMR (CDCl$_3$): 2.92 (t, 2H), 3.41 (t, 2H), 3.58–4.10 (m, 5H), 6.53 (d, 2H). 6.78 (d, 2H), 7.10–7.41 (m, 10H).

Example 3 a) (Z)-4-[4-(2-Imidazol-1-yl-ethoxy)phenyl]-3,4-dinhenyl-but-3-en-1-ol (Z)-4-[4-(2-Bromoethoxy)phenyl]-3,4-diphenylbut-3-en-1-ol (preparation described in U.S. Pat. No. 4,996,225) (4.97 g, 0.0117 mol) is dissolved in methyl ethyl ketone (50 ml) and potassium carbonate (4.8 g, 0.035 mol) and imidazole sodium salt (2.11 g, 0.0234 mol) is added to the solution. Mixture is stirred and refluxed for five hours. Then the solution is filtered and the filtrate is evaporated to dryness. The residue is dissolved in ethyl acetate, washed with 2 N aqueous sodium hydroxide solution and with water, dried and evaporated to dryness. The residue is recrystallized from the mixture of toluene and acetonitrile.

$^1$H NMR (CDCl$_3$): 2.75 (t, 2H), 3.59 (dist.t, 2H), 4.07 (dist.t, 2H), 4.23 (dist.t, 2H), 6.51 (d, 2H), 6.79 (d, 2H), 6.97 (s, 1H), 7.03 (s, 1H), 7.05–7.40 (m, 10H), 7.51 (s, 1H).

(Z)-4-[4-(2-Methylaminoethoxy)phenyl]3,4-diphenylbut-3-en-1-ol (Z)-4-[4-(2-Chloroethoxy)phenyl]-3,4-diphenylbut-3-en-1-ol (prepared as (Z)-4-[4-(2-bromoethoxy)phenyl]-3,4-diphenylbut-3-en-1-ol preparation of which is described in U.S. Pat. No. 4,996,225)(2.0 g, 0.0052 mol) and methyl amine in 40% aqueous solution (5 ml, 0.065 mol) is mixed with dimethylformamide (8 ml). Mixture is heated in a sealed tube at 60° C. for 8 hours. To the mixture is added 60 ml of water and extracted with ethyl acetate. Ethyl acetate phase is washed with aqueous 2 N hydrogen chloride solution. Water phase is made alkaline with 2 N sodium hydroxide solution and extracted with ethyl acetate. Ethyl acetate phase is washed with water, dried with magnesium sulfate and evaporated to dryness. Yield 1.5 g.

$^1$H NMR (CDCl$_3$): 2.39 (s, 3H), 2.70 (t, 2H), 2.84 (t, 2H), 3.48 (t, 2H), 3.93 (t, 2H), 6.59 (d, 2H), 6.77 (d, 2H), 7.10–7.40 (m, 10H).

b) (Z)-4-(4-{2-[(2-Benzyloxyethyl)methylamino] ethoxy}phenyl)-3,4-diphenyl-but-3-en-1-ol Prepared by using the same PTC method as in the example 1a using benzyl 2-bromoethyl ether as a reagent.

$^1$H NMR (CDCl$_3$): 2.35 (s, 3H), 2.70, 2.75, 2,79 (3 t, 6H1), 3.56 (t, 2H), 3.60 (t, 2H), 3.94 (t, 2H), 4.50 (s, 2H), 6.54 (d, 2H), 6.77 (d, 2H), 7.10–7.20 (m, 5H), 7.25–7.35 (m, 10H).

c) (Z)-1-{2-[4-(4-Chloro-1,2-diphenylbut-1-enyl) phenoxy]ethyl}-1H-imidazole No. 21)

is prepared according to the example 1d using triphenylphosphine and carbon tetrachloride as reagents. Purification of product is made by evaporating acetonitrile and dissolving the residue to acidic methanol-water (8:2) solution and extracting triphenylplhosphine with toluene (three times, at room temperature). Methanol-water-solution was made alkaline and the product was extracted with toluene. Toluene phase was washed twice with water and evaporated to dryness. The product was crystallized from ethyl acetate as HCl-salt. Yield 46%.

$^1$H NMR (HCl-salt, MeOH-d4): 2.89 (t, 2H), 3.39 (t, 2H), 4.23 (t, 2H), 4.60 (t, 2H), 6.60 (d, 2H), 6.80 (d, 2H), 7.10–7.40 (m, 10H ), 7.54 (s, 1H), 7.67 (s, 1H), 8.98 (s, 1H).

(Z)-(2-Benzyloxyethyl)-{2-[4-(4-chloro-1,2-diphenyl-but-1-enyl)phenoxy-ethyl}methylamine is prepared according to example 1d using thionyl chloride as a reagent.

$^1$H NMR (CDCl$_3$): 2.35 (s, 3H), 2.70, 2.79 (2 t, 4H), 2.92 (t, 2H), 3.42 (t, 2H), 3.56 (t, 2H), 3.93 (t, 2H), 4.51 (s, 2H), 6.54 (d, 2H), 6.77 (d, 2H), 7.10–7.40 (m,15H).

d) (Z)-2-({2-[-4-(4-Chloro-1,2-diphenyl-but-1-enyl) phenoxy]ethyl}-methylamino)ethanol (No. 22)

is prepared by the same method as 1e using Zn and acetyl chloride as reagents.

$^1$H NMR (CDCl$_3$): 2.32 (s, 3H), 2.60 (t, 2H), 2.78 (t, 2H), 2.92 (t, 2H), 3.42 (t, 2H), 3.57 (t, 2H), 3.91 (t, 2H), 6.54 (d, 2H), 6.78 (d, 2H), 7.05–7.40 (m, 10H).

Example 4 a) 2-(4-Chlorophenyl)-1-(4-methoxyphenyl) ethanone

Anisole (13.9 g, 0.13 mol) is added to a stirred solution of 4-chlorophenylacetic acid (20.0 g, 0.12 mol) in trifluoroacetic anhydride (16.5 ml, 0.12 mol). The mixture is stirred in room temperature for 24 h. Ice water is added and the crystallized product is collected on a sinter and washed with water. The product is recrystallized from ethanol. The yield is 20.4 g, 67%.

$^1$H NMR (CDCl$_3$): 3.86 (s, 3H), 4.20 (s, 2H), 6.93 (d, 2H), 7.20 (d, 2H), 7.28 (d, 2H), 7.98 (d, 2H).

Using the same method the following compounds are prepared:

2-(4-Fluorophenyl)-1-(4-methoxyphenyl)ethanone $^1$H NMR (CDCl$_3$): 3.87 (s, 3H), 4.21 (s, 2H), 6.94 (d, 2H), 7.01 (t, 2H), 7.22 (dd, 2H), 7.99 (d, 2H).

1-(4-Methoxyphenyl)-2-phenyl-ethanone $^1$H NMR (CDCl$_3$): 3.84 (s, 3H), 4.23 (s, 2H), 6.92 (d, 2H), 7.20–7.40 (m, 5H), 7.99 (d, 2H).

b) 2-(4-Chlorophenyl)-1-(4-hydroxyphenyl)ethanone

Aluminum chloride (29.8 g, 0.223 mol) is added in small portions to a stirred solution of 2-(4-chlorophenyl)-1-(4-methoxyphenyl)ethanone (19.4 g, 0.074 mol) in toluene (300 ml). The mixture is heated to 60° C. and stirring is continued for 2 h. Dilute hydrochloric acid is added to the cooled mixture. Ethyl acetate is added to dissolve the product. The layers are separated and the aqueous phase is extracted with ethyl acetate. The combined organic phases are dried and the solvents are evaporated. The product is recrystallized from toluene. The yield is 17 g, 93%.

$^1$H NMR (CDCl$_3$+MeOH-d$_4$): 4.19 (s, 2H), 6.85 (d, 2H), 7.19 (d, 2H), 7.28 (d, 2H), 7.90 (d, 2H).

Using the same method the following compounds are prepared:

2-(4-Fluorophenyt)-1-(4-hydroxyphenyl)ethanone $^1$H NMR (CDCl$_3$+MeOH-d$_4$): 4.20 (s, 2H), 6.86 (d, 2H), 7.00 (t, 2H), 7.22 (dd, 2H), 7.91 (d, 2H).

1-(4-Hydroxyphenyl)-2-phenyl ethanone $^1$H NMR (CDCl$_3$+MeOH-d$_4$): 4.20 (s, 2H), 6.84 (d, 2H), 7.2–7.4 (m, 5H) 7.90 (d, 2H).

c) O-Alkylation of 4-hydroxydesoxybenzoin Derivatives

In PTC-conditions 2-(4-Chlorophenyl)-1-[4-(2-dimethylaminoethoxy)phenyl]ethanone 10% Aqueous sodium hydroxide is added to the mixture containing 2-(4-chlorophenyl)-1-(4-hydroxyphenyl) ethanone (6.0 g, 0.024 mol), TBABr (0.9 g) in toluene (60 ml) at 60° C. The mixture is stirred for 30 min. N,N-Dimethylaminoethyl chloride hydrochloride (3.6 g, 0.025 mol) is added and stirring is continued at 70–75° C. for 3 h. The layers are separated and the aqueous phase is extracted with toluene. The combined toluene phases are evaporated to give the product (1.85 g, 24%)

$^1$H NMR (CDCl$_3$): 2.34 (s, 6H), 2.75 (t, 2H), 4.12 (t, 2H), 4.20 (s, 2H), 6.95 (d, 2H), 7.19 (d, 2H), 7.29 (d, 2H), 7.97 (d, 2H).

Using the same method the following compound is prepared:

1-[4-(2-Dimethylaminoethoxy)phenyl]-2-(4-fluorophenyl)ethanone $^1$H NMR (CDCl$_3$): 2.34 (s, 6H), 2.75 (t, 2H), 4.12 (t, 2H), 4.21 (s, 2H), 6.96 (d, 2H), 7.01 (t, 2H), 7.22 (dd, 2H), 7.98 (d, 2H).

With K$_2$CO$_3$ in 2-butanone

1-[4-(2-Benzyloxyethoxy)phenyl]-2-phenyl ethanone 1-(4-Hydroxyphenyl)-2-phenyl ethanone (17 g, 0.08 mol) is dissolved in 2-butanone (200 ml) and potassium carbonate (33.1 g, 0.24 mol) and 2-benzyloxyethyl bromide (25.8 g, 0.12 mol) is added to the solution. Mixture is stirred and refluxed for three hours. Then the solution is filtered and the filtrate is evaporated to dryness. The residue is dissolved in toluene, washed with 2 N aqueous sodium hydroxide solution and with water, dried and evaporated to dryness. The product is crystallized from ethanol. Yield 23.2 g, 84%.

$^1$H NMR (CDCl$_3$): 3.80–3.86 (m, 2H), 4.20–4.22 (m, 2H), 4.23 (s, 2H), 4.63 (s, 2H), 6.90 (d, 2H), 7.20–7.40 (m, 10H), 7.90 (d, 2H).

Using the same method the following compounds are prepared:

1-[4-(2-Benzyloxyethoxy)phenyl]-2-(4-chlorophenyl)ethanone $^1$H NMR (CDCl$_3$): 3.84 (dist.t., 2H), 4.20 (dist.t., 2H), 4.20 (s, 2H), 4.63 (s, 2H), 6.95 (d, 2H), 7.19 (d, 2H), 7.29 (d, 2H), 7.30–7.45 (m, 5H), 7.96 (d, 2H).

2-(3-Methoxyphenyl)-1-[4-(2-piperidin-1-ylethoxy)phenyl]ethanone 1-(4-hydroxyphenyl)-2-(3-methoxyphenyl)ethanone and 1-(2-chloroethyl)piperidine hydrochloride are used as starting materials.

$^1$H NMR (CDCl$_3$): 1.37–1.52 (m, 2H), 1.52–1.68 (m, 4H), 2.50 (br.t, 4H), 2.78 (t, 2H), 3.77 (s, 3H), 4.14 (t, 2H), 4.19 (s, 2H), 6.73–6.90 (m, 3H), 6.90 (d, 2H), 7.22 (t, 1H), 7.96 (d, 2H).

2-(2-Methoxyphenyl)-1-[4-(2-piperidin-1-ylethoxy)phenyl]ethanone 1-(4-hydroxyphenyl)-2-(2-methoxyphenyl)ethanone and 1-(2-chloroethyl)piperidine hydrochloride are used as starting materials.

$^1$H NMR (CDCl$_3$): 1.40–1.53 (m, 2H), 1.53–1.70 (m, 4H), 2.51 (br.t, 4H), 2.79 (t, 2H), 3.79 (s, 3H), 4.16 (t, 2H), 4.22 (s, 2H), 6.84–7.00 (m, together 4H) under which 6.92 (d, 2H), 7.14–7.30 (m, 2H), 8.00 (d, 2H).

d) C-Alkylation of Desoxybenzoin Derivatives

4-Benzyloxy-2-(4-chlorophenyl)-1-[4-(2-dimethylaminoethoxy)phenyl]butan-1-one

The mixture containing 2-(4-chlorophenyl)-1-4-(2-dimethylaminoethoxy)phenyl]-ethanone (6.3 g, 0.020 mol) and TBABr (0.5 g) in toluene (70 ml) is heated to 70° C. and 48% aqueous sodium hydroxide (70 ml) is added. The mixture is stirred for 30 min. and (2-bromoethoxymnethyl)benzene (5.5 g, 0.025 mol) is added dropwise at 85–90° C. The reaction mixture is stirred at 95–100° C. for 3 h. The layers are separated and the aqueous phase is extracted with toluene. The combined organic phases are washed with water and the solvent is evaporated. The residual product (9.0 g ) is used in the next reaction step without further purification.

$^1$H NMR (CDCl$_3$): 1.93–2.15 and 2.38–2.58 (2m, together 2H), 2.32 (s, 6H1), 2.72 (t, 2H), 3.25–3.55 (m, 2H), 4.08 (t, 2H), 4.42 (s, 2H), 4.82 (t, 1H), 6.88 (d, 2H), 7.15–7.40 (m, 9H), 7.92 (d, 2H).

Using the same method the following compounds are prepared:

4-Benzyloxy-1-[4-(2-dimethylaminoethoxy)phenyl]-2-(4-fluorophenyl)butan-1-one $^1$H NMR (CDCl$_3$): 1.95–2.15 and 2.40–2.60 (2m, together 2H), 2.31 (s, 6H), 2.71 (t, 2H), 3.25–3.55 (m, 2H), 4.07 (t, 2H), 4.42 (s, 2H), 4.83 (t, 1H), 6.88 (d, 2H), 6.94 (t, 2H ), 7.10–7.40 (m, 7H), 7.93 (d, 2H).

4-Benzyloxy-2-(4-chlorophenyl)-1-(4-methoxyphenyl)butan-1-one $^1$H NMR (CDCl$_3$): 1.95–2.15 and 2.35–2.55 (2m, together 2H), 3.30–3.55 (m, 2H), 3.82 (s, 3H), 4.42 (s, 2H), 4.82 (t, 1H), 6.85 (d, 2H), 7.10–7.40 (m, 9H), 7.93 (d, 2H).

1-[4-(2-Benzyloxyethoxy)phenyl]-2-phenyl-4-(tetrahydropyranyloxy)butan-1-one $^1$H NMR (CDCl$_3$): 1.4–1.9 (m, 6H), 2.0–2.2 (m, 1H), 2.4–2.65 (m, 1H), 3.2–4.05 (m, 6H), 4.1–4.2 (m, 2H), 4.45–4.5 (m, 1H), 4.60 (s, 2H), 4.80 (t, 1H), 6.88 (d, 2H), 7.1–7.4 (m, 10H), 7.96 (d, 2H).

1-[4-(2-Benzyloxyethoxy)phenyl]-2-(4-chloroplienyl)-4-(tetralydropyranyloxy)butan-1-one $^1$H NMR (CDCl$_3$): 1.30–1.90 (m, 6H), 1.95–2.15 and 2.38–2.58 (2m, together 2H), 3.20–4.05 (m, 6H), 4.16 (dist.t., 2H), 4.75–4.85 (m, 1H), 4.61 (s, 2H), 4.80 (t, 1H), 6.88 (d, 2H), 7.13–7.40 (m, 9H ), 7.94 (d, 2H).

1,2-Bisphenyl-4-(tetrahydropyranyloxy)butan-1-one $^1$H NMR (CDCl$_3$): 1.4–1.9 (m, 6H), 2.0–2.2 (m, 1H), 2.4–2.65 (m, 1H), 3.2–3.9 (m, 4H), 4.45–4.5 (m, 1H), 4.85 (t, 1H), 7.1–7.5 (m, 8H), 8.00 (d, 2H).

2-(3-Methoxyphenyl)-1-[4-(2-piperidin-1-ylethoxy)phenyl]-4-(tetrahydropyranyloxy)butan-1-one $^1$H NMR (CDCl$_3$): 1.40–1.90 (m, 13:H), 1.95–2.2 (m, 1H), 2.48 (br.t, 4H), 2.75 (t, 2H), 3.20–3.90 (m, 4H) under which 3.76 (s, 3H), 4.11 (t, 2H), 4.49 (m, 1H), 4.77 (m, 1H), 6.73 (dd, 2H), 6.80–6.95 (m, 4H), 7.21 (t, 1H), 7.96 (d, 2H).

2-(2-Methoxyphenyl)-1-[4-(2-piperidin-1-ylethoxy)phenyl]-4-(tetrahydropyranyloxy)butan-1-one $^1$H NMR (CDCl$_3$): 1.30–1.90 (m, 13H), 1.95–2.15 (m, 1H), 2.48 (m, 4H), 2.74 (t, 2H), 3.20–4.00 (m, 4H) under which 3.88 (s, 3H), 4.09 (t, 2H), 4.45–4.55 (m, 1H), 5.22 (m, 1H), 6.73–6.90 (m, 4H) 7.14–7.30 (m, 2H), 7.97 (d, 2H).

e) Gripnard Reaction With Desoxybenzoin Derivatives

4-Benzyloxy-2-(4-chlorophenyl)-1-[4-(2-dimethylaminoethoxy)-phenyl]-1-phenylbutan-1-ol 4-Benzyloxy-2-(4-chlorophenyl)-1-[4-(2-dimethylaminoethoxy)phenyl]butan-1-one (9.4 g, 0.021 mol) is added to Grignard reagent prepared from bromobenzene (13.1 g, 0.083 mol) and Mg turnings (2.0 g, 0.083 mol) in dry tetrahydrofuran. The mixture is refluxed for 3 h. Saturated ammonium chloride solution is added to the cooled reaction mixture, the THF layer is separated and the aqueous phase is extracted with toluene. The combined organic phases are washed with water and the solvents are evaporated. The residual product (10.7 g) is used in the next reaction step without further purification.

Using the same method the following compounds are prepared:

4-Benzyloxy-1-[4-(2-dimethylaminoethoxy)phenyl]-2-(4-fluorophenyl-1-phenylbutan-1-ol
is used in the next reaction step without further purification
4-Benzyloxy-2-(4-chlorophenyl)-]-[4-(2-dimethylaminoethoxy)phenyl]-1-(4-methoxyphenyl)butan-1-ol
is used in the next reaction step without further purification
1-(3-Benzyloxyphenyl)-1-[4-(2-benzyloxyethoxy)phenyl]-2-phenyl]-4-(tetrahydropyranyloxy)butan-1-ol
is used in the next reaction step without further purification.
1-[4-(Benzyloxyethoxy)phenyl]-2-(4-chlorophenyl)-1-(4-methoxyphenyl)-4-(tetrahydropyranyloxy)butan-1-ol
is used in the next reaction step without further purification.
2-(3-Methoxyphenyl)-1-phenyl-1-[4-(2-piperidin-1-ylethoxy)phenyl]-4-(tetrahydropyranyloxy)butan-1-ol
is used in the next reaction step without further purification.
2-(2-Methoxyphenyl)-1-phenyl-1-[4-(2-piperidin-1-ylethoxy)phenyl]-4-(tetrahydropyranyloxy)butan-1-ol
is used in the next reaction step without further purification.
1-[3-(2-Dimethylaminoethoxy)phenyl]-1,2-diphenyl-4-(tetrahydropyranyloxy)butan-1-ol
is used in the next reaction step without further purification.
1-[4-(2-Benzyloxyethylsulfanyl)phenyl]-1,2-diphenyl-4-(tetrahydropyranyloxy)butan-1-ol
is used in the next reaction step without further purification.
1-[4-(2-Dimethylaminoethylsulfanyl)phenyl]-1,2-diphenyl-4-(tetrahydropyranyloxy)butan-1-ol
is used in the next reaction step without further purification f) Dehydration of the Triarylbutandiol Derivatives (2-{4-[4-Benzyloxy-2-(4-chlorophenyl)-1-phenylbut-1-enyl]-phenoxy}ethyl)dimethylamine 4-Benzyloxy-2-(4-chlorophenyl)-1-[4-(2-dimethylaminoethoxy)phenyl]-1-phenylbutan-1-ol (10.7 g) is dissolved in methanol (70 ml) and concentrated hydrochloric acid is added to make the solution acidic. The mixture is stirred for 4.5 h at room temperature and then at 50° C. for 1 h. The solvent is evaporated and the product is purified by flash chromatography (eluent toluene:triethylamine 24:1). The yield is 5.6 g as a mixture of E- and Z-isomers (1:2).

$^1$H NMR (mixture of Z- and E-isomers, CDCl$_3$): 2.28 and 2.34 (2s, 6H:), 2.64 and 2.73 (2t, 24H), 2.78 and 2.83 (2t, 2H), 3.40 and 3.42 (2t, 2H), 3.93 and 4.07 (2t, 2H), 4.36 and 4.38 (2s, 2H), 6.55–7.40 (m, 18H) from which can be identified 6.58 and 6.75 (2d, 4H).

Using the same method the following compounds are prepared:

(2-{4-[4-Benzyloxy-2-(4-fluorophenyl)-1-phenylbut-1-enyl]phenoxy}-ethyl)dimethylamine $^1$H NMR (mixture of Z- and E-isomers, CDCl$_3$): 2.28 and 2.34 (2s, 6H), 2.65 and 2.74 (2t, 2H), 2.78 and 2.83 (2t, 2H), 3.41 and 3.43 (2t, 2H), 3.93 and 4.07 (2t, 2H), 4.37 and 4.39, (2s, 2H), 6.50–7,40 (m, 18H) from which can be identified 6.58 and 6.75 (2d, 4H).

(2-{4-[4-Benzyloxy-2-(4-chlorophenyl)-1-(4-methoxyphenyl)but-1-enyl]phenoxy}-ethyl)dimethylamine $^1$H NMR (mixture of Z- and E-isomers, CDCl$_3$): 2.30 and 2.35 (2s, 6H), 2.67 and 2.76 (2t, 2H), 2.81 (t, 2H), 3.41 (t, 2H), 3.69 and 3.81 (2s, 3H), 4.38 (s, 2H), 6.56 and 6.86 (2d, 2H), 6.58 and 6.85 (2d, 2H), 6.75 (d, 2H), 6.76 (d, 2H), 7.0–7.4 (m, 11H).

4-[4-(2-Benzyloxyethoxy)phenyl]-3-(4-chlorophenyl)-4-(4-methoxyphenyl)but-3-en-1-ol is prepared according to the procedure of the example 1c. The Z- and E-isomers are separated by flash chromatography, eluent toluene:metanol 99:1.

Z-isomer $^1$H NMR (CDCl$_3$): 2.76 (t, 2H), 3.57 (br.t, 2H), 3.75 (dist.t, 2H), 3.81 (s, 3H), 4.03 (dist.t, 2H), 4.59 (s, 2H), 6.59 (d, 2H), 6.76 (d, 2H), 6.87 (d, 2H), 7.05 (d, 2H), 7.13 (d, 2H), 7.19 (d, 2H), 7.27–7.40 (m, 5H).

E-isomer $^1$H NMR (CDCl$_3$): 2.76 (t, 2H), 3.58 (br.t, 2H), 3.70 (s, 3H), 3.84 (dist.t, 2H), 4.17 (dist.t, 2H), 4.65 (s, 2H), 6.57 (d, 2H ), 6.77 (d, 2H), 6.90 (d, 2H), 7.06 (d, 2H), 7.15 (d, 2H), 7.18 (d, 2H), 7.27–7.40 (m, 5H).

Using the same method the following compounds are prepared.

3-(3-Methoxyphenyl)-4-phenyl-4-[4-(2-piperidin-1-ylethoxy)phenyl]but-3-en-1-ol

Z-isomer: $^1$H NMR (CDCl$_3$): 1.33–1.50 (m, 2H), 1.50–1.65 (m, 4H), 2.45 (br.t., 4H), 2.67 (t, 2H), 2.73 (t, 2H, ), 3.58 (t, 2H), 3.65 (s, 3H ), 3.96 (t, 2H), 6.55 (d, 2H), 6.63–6.77 (m, 3H), 6.79 (d, 2H), 7.10 (t, 1H), 7.20–7.40 (m, 5H).

E-isomner: $^1$H NMR (CDCl$_3$): 1.40–1.55 (m, 2H), 1.55–1.70 (m, 4H), 2.51 (br.t., 4H), 2.77 (t, 2H), 2.80 (t, 2H), 3.61 (s, 3H), 3.62 (t, 2H), 3.94 (t, 2H), 6.6–7.25 (m, 13H).

3-(2-Methoxyphenyl)-4-phenyl-4-[4-(2-piperidin-1-ylethoxy)phenyl]but-3-en-1-ol

Z-isomer: $^1$H NMR (CDCl3): 1.33–1.48 (m, 2H), 1.48–1.65 (m, 4H), 2.43 (br.t., 4H), 2.20–2.50 (t, 2H), 2.65 (t, 2H), 3.43–3.60 (t, 2H), 3.62 (s, 3H), 3.93 (t, 2H), 6.52 (d, 2H), 6.70–6.90 (m, 2H) under which 6.82 (d, 2H), 7.05–7.43 (m, 7H).

E-isomer: $^1$H NMR (CDCl$_3$): 1.38–1.52 (m, 2H), 1.52–1.70 (m, 4H), 2.51 (br.t., 4H), 2.38–2.58 (t, 2H), 2.77 (t, 2H), 3.59 (s, 3H ), 3.45–3.65 (m, 2H), 4.10 (t, 2H), 6.6–7.35 (m, 13H).

(E)-4-(3-Benzyloxyphenyl)-4-[4-(2-benzyloxyethoxy) phenyl]-3-phenyl-but-3-en-1-ol $^1$H NMR (CDCl$_3$): 2.73 (t, 2H), 3.5–3.6 (m, 2H), 3.7–3.76 (m, 2H), 4.0–4.03 (m, 2H), 4.60 (s, 2H), 5.05 (s, 2H), 6.56 (d, 2H), 6.78 (d, 2H), 6.8–6.95 (m, 2H), 7.05–7.35 (m, 17H).

(Z)-4-[4-(2-Benzyloxyethyl sulfanyl)phenyl]-3,4-diphenyl-but-3-en-1-ol $^1$H NMR (CDCl$_3$): 2.75 (t, 2H), 3.02 (t, 2H), 3.56 (t, 4H), 4.47 (s, 2H), 6.78 (d, 2H), 6.96 (d, 2H), 7.1–7.4 (m, 15H).

(Z)-4-[4-(2-Dimethylaminoethylsulfanyl)pheny]3,4-diphenyl-but-3-en-1-ol

MS: EI, m/e 403 (M$^-$, 1%), 332 (1%), 72 (12%), 58 (100%).

5 g) Removal of the Protecting Benzyl Group
3-(4-Chlorophenyl)-4-[4-(2-dimethylaminoethoxy)phenyl]-4-phenylbut-3-en-1-ol (2-{4-[4-Benzyloxy-2-(4-chlorophenyl)-1-phenylbut-1-enyl]phenoxy}ethyl)dimethylamine (1.1 g, 2.1 mmol) is dissolved in toluene, Zn powder (0.4 g, 6.1 mmol) and acetyl chloride (0.6 g, 7.6 mmol) are added and the mixture is stirred at 40° C. for 3 h. Additional Zn (0.5 g) and acetyl chloride (0.6 g) are added and stirring is continued for another 5 h. Ethyl acetate is added and the precipitate is filtered off. The solvents are evaporated and the residue is dissolved in methanol. The acetate ester of the product is hydrolyzed by making the mixture alkaline with 48% aqueous sodium hydroxide and stirring the mixture at room temperature for 2 h. Methanol is evaporated, the residue is dissolved in toluene and washed with water. Toluene is evaporated and the isomers of the product are separated by flash chromatography. The yield of the Z-isomer is 0.25 g and of the E-isomer 0.15 g.

Z-isomer: $^1$H NMR (CDCl$_3$): 2.28 (s, 6H), 2.65 (t, 2H), 2.72 (t, 2H), 3.57 (t, 2H), 3.94 (t, 2H), 6.58 (d, 2H), 6.76 (d, 2H), 7.07 (d, 2H), 7.15 (d, 2H), 7.20–7.40 (m, 5H).

E-isomer: $^1$H NMR (CDCl$_3$): 2.34 (s, 6H), 2.74 (t, 2H), 2.78 (t, 2H), 3.59 (t, 2H), 4.07 (t, 2H), 6.80–7.30 (m, 13H).

Using the same method the following compounds are prepared:

4-[4-(2-Dimethylaminoethoxy)phenyl]-3-(4-fluorophenyl)-4-phenylbut-3-en-1-ol

Z-isomer: $^1$H NMR (CDCl$_3$): 2.27 (s, 6H), 2.64 (t, 2H), 2.72 (t, 2H), 3.56 (t, 2H), 3.93 (t, 2H), 6.56 (d, 2H), 6.76 (d, 2H), 6.86 (t, 2H), 7.00–7.40 (m, 7H).

E-isomer: $^1$H NMR (E-isomer, CDCl$_3$): 2.35 (s, 6H), 2.75 (t, 2H), 2.78 (t, 2H), 3.60 (t, 2H), 4.08 (t, 2H), 6.75–7.40 (m, 13H).

3-(4-Chlorophenyl)-4-[4-(2-dimethylaminoethoxy)phenyl]-4-(4-methoxyphenyl)but-3-en-1-ol Z-isomner: $^1$H NMR (CDCl$_3$): 2.28 (s, 6H), 2.65 (t, 2H), 2.75 (t, 2H), 3.57 (t, 2H), 3.81 (s, 3H), 3.94 (t, 2H), 6.58 (d, 2H), 6.75 (d, 2H), 6.87 (d, 2H), 7.05 (d, 2H), 7.13 (d, 2H), 7.19 (d, 2H).

E-isomner: $^1$H NMR (CDCl$_3$): 2.33 (s, 6H), 2.74 (t, 2H), 2.75 (t, 2H), 3.56 (t, 2H), 3.69 (s, 3H), 4.07 (t, 2H), 6.56 (d, 2H), 6.76 (d, 2H), 6.88 (d, 2H), 7.06 (d, 2H), 7.13 (d, 2H), 7.17 (d, 2H).

h) Conversion of the Hydroxyl Group to Chlorine
(Z)-(2-{4-[4-Chloro-2-(4-chloropheny 1)-1-phenylbut-1-enyl]phenoxy}dimethylamine (No. 23)

(Z)-3-(4-Chlorophenyl)-4-[4-(2-dimethylaminoethoxy)phenyl]-4-phenylbut-3-en-1-ol (0.22 g, 0.5 mmol) is dissolved in toluene. Thionyl chloride (0.2 g, 1.7 mmol) is added and the mixture is refluxed for 45 min. Toluene is partly evaporated and the precipitated hydrochloride salt of the product is filtered. The yield is 0.2 g.

$^1$H NMR (HCl salt, CDCl$_3$): 2.88 and 2.90 (s, together 6H), 2.91 (t, 2H), 3.40 (m, 4H), 4.40 (m, 2H), 6.58 (d, 2H), 6.81 (d, 2H), 7.07 (d, 2H), 7.19 (d, 2H), 7.20–7.50 (m, 5H).

Using the same method the following compounds are prepared:

(E)-(2-{4-[4-Chloro-2-(4-chlorophenyl)-1-phenylbut-1-enyl]phenoxy}ethyl)dimethylamine (No. 24)

$^1$H NMR (HCl salt, CDCl$_3$): 2.35–3.02 (m, 2H), 2.95 (s, 6H), 3.35–3.55 (m, 4H), 4.46–4.60 (m, 2H), 6.75–7.30 (m, 13H).

(Z)-(2-{4-[4-Chloro-2-(4-fluorophenyl)-1-phenylbut-1-enyl]phenoxy}-ethyl)dimethylamine (No. 25)

$^1$H NMR (HCl salt, CDCl$_3$): 2.88 (s, 6H), 2.94 (t, 2H, ), 3.41 (m, 4H), 4.39 (m, 2H), 6.56 (d, 2H), 6.80 (d, 2H), 6.91 (t, 2H), 7.10 (dd, 2H), 7.20–7.40 (m, 5H).

2-{4-[4-Chloro-2-(4-chlorophenyl)-1-(4-methoxyphenyl)but-1-enyl]phenoxy}-ethyl)dimethylamine (No. 26 and 27)

Z-isomer (No. 26): $^1$H NMR (HCl salt, CDCl$_3$ +MeOH-d$_4$): 2.89 (s, 6H), 2.94 (t, 2H), 3.41 (m, 4H), 3.84 (s, 3H), 4.34 (m, 2H), 6.59 (d, 2H), 6.81 (d, 2H), 6.90 (d, 2H), 7.06 (d, 2H), 7.18 (d, 2H), 7.19 (d, 2H).

E-isomer (No. 27): $^1$H NMR (HCl salt, CDCl$_3$+MeOH-d$_4$): 2.91 (t, 2H), 2.98 (s, 6H), 3.41 (t, H), 3.54 (m, 2H), 3.71 (s, 3H), 4.45 (m, 2H), 6.59 (d, 2H), 6.77 (d, 2H), 6.94 (d, 2H), 7.06 (d, 2H), 7.17–7.18 (d, 2H), 7.23 (d, 2H).

1-(2-{4-[4-Chloro-2-(3-methoxyphenyl)-1-phenylbut-1-enyl]phenoxy}-ethyl)piperidine (No. 28 and 29)

Z-isomer (No. 28): $^1$H NMR (HCl salt, MeOH-d$_4$): 1.45–2.10 (m, 6H), 2.92 (t, 2H), 3.06 (dt, 2H), 3.44 (t, 2H), 3.47–3.66 (m, 4H), 3.68 (s, 3H), 4.27 (dist.t., 2H), 6.70–6.85 (m, 5H), 6.92 (d, 2H), 7.15 (dt, 1H), 7.30–7.50 (m, 5H).

E-isomer (No. 29): $^1$H NMR (HCl salt, MeOH-d$_4$): 1.45–2.15 (m, 6H), 2.96 (t, 2H), 3.12 (dt, 2H), 3.47 (t, 2H), 3.58–3.75 (m, 4H), 3.62 (s, 3H), 4.44 (dis.t., 2H, 6.65–6.83 (m, 3H), 6.90–6.97 (m, 2H), 7.01–7.18 (m, 6H), 7.31 (d, 2H).

1-(2-{4-[4-Chloro-2-(2-methoxyphenyl)-1-phenylbut-1-enyl]phenoxy}-ethyl)piperidine (No. 30 and 31)

Z-isomer (No. 30): $^1$H NMR (HCl salt, MeOH-d4): 1.50–2.05 (m, 6H), 2.88 (t, 2H), 3.05 (dt, 2H), 3.41 (t, 2H), 3.45–3.65 (m, 4H), 3.86 (s, 3H), 4.25 (dis.t., 2H), 6.65–6.79 (m, 3H), 6.88–7.00 (m, 4H ), 7.20 (dt, 1H), 7.30–7.50 (m, 5H).

E-isomer (No. 31): $^1$H NMR (HCl salt, MeOH-d$_4$): 1.55–2.20 (m, 6H), 2.92 (t, 2H), 3.13 (dt, 2H), 3.43 (t, 2H), 3.58–3.75 (m, 4H), 3.84 (s, 3H), 4.45 (dist.t., 2H), 6.73 (dt, 1H), 6.89–7.30 (m, 7H), 7.08 (d, 2H), 7.18 (dt, 1H), 7.32 (d, 2H).

(Z)-1-[4-(2-Benzyloxyethylsulfanyl)phenyl]-1,2-diphenyl-4-chloro-but-1-ene $^1$H NMR (CDCl$_3$): 2.92 (t, 2H), 3.02 (t, 2H), 3.41 (t, 2H), 3.56 (t, 2H), 4.47 (s, 2H), 6.78 (d, 2H), 6.96 (d, 2H), 7.10–7.40 (m, 15H).

(Z)-1-[4-(2-Dimethylaminoethylsulfanyl)phenyl]-1,2-diphenyl-4-chloro-but-1-ene (No. 32)

$^1$H NMR (CDCl$_3$): 2.28 (s, 6H), 2.46 (dist.t, 2H), 2.85–2.95 (m, 4H), 3.41 (dist.t, 2H), 6.79 (d, 2H), 6.96 (d, 2H), 7.00–7.40 (m, 10H).

1-[4-(2-Benzyloxyethoxy)phenyl]-4-chloro-2-(4-chlorophenyl)-1-(4-methoxyphenyl)but-1-ene Z-isomer, $^1$H NMR (CDCl$_3$): 2.93 (t, 2H), 3.41 (t, 2H), 3.83 (s, 2H), 3.76 (dist.t,2H), 4.04 (dist.t, 2H), 4.59 (s, 2H), 6.59 (d, 2H), 6.77 (d, 2H), 6.87 (d, 2H), 7.05 (d, 2H), 7.15 (d, 2H), 7.19 (d, 2H), 7.27–7.40 (m, 5H).

E-isomer $^1$H NMR (CDCl$_3$): 2.93 (t, 2H), 3.41 (t, 2H), 3.70 (s, 3H), 3.85 (dis.t, 2H), 4.18 (dist.t, 2H), 4.65 (s, 2H), 6.57 (d, 2), 6.79 (d, 2H, 6.92 (2), 7.06 (d, 2H), 7.16 (d, 2H), 7.18 (d, 2H), 7.27–7.40 (m, 5H).

(E)-1-(3-Benzyloxyphenyl)-1-[4-(2-benzyloxyethoxy)phenyl]-4-chlorophenyl-but-1-ene The compound is prepared by using the method described in the examples 1d using Ph$_3$P and CCl$_4$ as reagents.

$^1$H NMR (CDCl$_3$): 2.93 (t, 2H), 3.40 (t, 2H), 3.71–3.76 (m, 2H), 3.98–4.05 (m, 2H), 4.58 (s, 2H), 5.06 (s, 2H), 6.60 (d, 2H), 6.78 (d, 2H), 6.85–7.50 (m, 19H).

(Z)-{2-[3-(4-Chloro-1,2-diphenylbut-1-enyl)phenoxy]ethyl}dimethylamine (No. 33)

1-[3-(2-Dimethylaminoethoxy)phenyl]-1,2-diphenyl-4-(tetrahydropyranyloxy)-butan-1-ol (0.93 g, 1,9 mmol) is dissolved in toluene (10 ml). Triethylamine (1.9 mmol) is added to the solution and the mixture is cooled to −10° C.

Thionylchloride (5.8 mmol) is added to the mixture at −10−±0° C. The mixture was stirred for 1 hour at 0–5° C., warmed up to 80° C. and stirred at this temperature for 3 hours. Solvent was evaporated, the residue was dissolved to toluene, washed with 2 N NaOH and with water. The Z-isomer of the product was crystallized from ethyl acetate as HCl salt. Yield 0.15 g $^1$H NMR (HCl salt, CDCl$_3$): 2.79 (s, 6H), 2.94 (t, 2H), 3.20–3.29 (m, 2H), 3.42 (t, 2H), 4.12–4.20 (m, 2H), 6.40 (s, 1H), 6.51–6.62 (m, 2H), 6.98 (t, 1H), 7.10–7.45 (m, 10H).

i) Removal of the Protecting Groups (E)-3-{4-Chloro-1-[4-(2-hydroxyethoxy)phenyl]-2-phenyl-but-1-enyl}-phenol (No. 34)

E)-4-(3-Benzyloxyphenyl)-4-[4-(2-benzyloxyethoxy) phenyl]-4-chloro-3-phenyl-but-1-ene (1.95 g, 3.39 mmol) is hydrogenated in etlhanol-etlhyl acetate (5 ml:20 ml) containing triethylamine (3.4 mmol) and 10% palladium on carbon (0.195 g) as a catalyst. The catalyst is filtered off and the solvent is evaporated. The product is purified with flash chromatography and crystallized from toluene-methanol (9:1). Yield 0.23 g.

$^1$H NMR (CDCl$_3$+MeOH-d$_4$): 2.95 (t, 2H), 3.42 (t, 2H), 3.8–4.0 (m, 4H), 6.56 (d, 2H), 6.75–6.82 (m, 4H), 7.10–7.25 (m, 7H).

Using the same method the following compound included in the invention is prepared:

(Z)-3-[4-(4-Chloro-1 ,2-diphenylbut-1-enyl)phenoxy] propan-1-ol (No. 35)

$^1$H NMR (CDCl$_3$): 1.96 (quint., 2H), 2.92 (t, 2H), 3.42 (t, 2H), 3.80 (q, 2H), 3.989 (t, 2H), 6.55 (d, 2H), 6.78 (d, 2H), 7.11–7.40 (m, 10H).

(Z)-2-[4-(4-Chloro-1,2-diphenyl-but-1-enyl)-phenylsulfanyl]ethanol (No. 36)

is prepared according to the procedure of the example 2 g.

$^1$H NMR (CDCl$_3$): 2.93 (t, 2H), 3.00 (t, 2H), 3.41 (t, 2H), 3.64 (t, 2H), 6.81 (d, 2H), 7.01 (d, 2H), 7.10–7.40 (m, 10H).

Using the same method the following compound included in the invention is prepared.

(Z)-2-{4-[4-Chloro-2-(4-chlorophenyl)-1-(4-methoxyphenyl)but-1-enyl]-phenoxy}ethanol (No. 37)

$^1$H NMR (CDCl$_3$): 2.94 (t, 2H), 3.41 (t, 2H), 3.83 (s, 3H), 3.85–4.00 (m, 4H), 6.59 (d, 2H), 6.78 (d, 2H), 6.90 (d, 2H), 7.06 (d, 2H), 7.16 (d, 2H), 7.19 (d, 2H).

Example 5 a) 1-[4-(2-Chloroethoxy)phenyl]-2-(2-chlorophenyl) ethanone

1-[4-(2-Chloroethoxy)phenyl]-2-(2-chlorophenyl) ethanoe is prepared according to the method described in the example 4a using 2-chloroethoxybenzene and 2-chlorophenylacetic acid as starting materials.

$^1$H NMR (CDCl$_3$): 3.85 (t, 2H), 4.30 (t, 2H), 4.39 (s, 2H), 6.98 (d, 2H), 7.22–7.26 (m, 3H), 7.39–7.50 (m, 1H), 8.04 (d, 2H).

Using the same method the following compound is prepared:

1-[4-(2-Chloroethoxy)phenyl]-2-phenylethanone $^1$H NMR (CDCl$_3$): 3.83 (t, 2H), 4.24 (s, 2H), 4.28 (t, 2H), 6.94 (d, 2H), 7.2–7.4 (m, 5H), 8.00 (d, 2H).

b) 2-(2-Chlorophenyl)-1-[4-(2-piperidinylethoxy) phenyl]ethanone

The mixture of 1-[4-(2-chloroethoxy)phenyl]-2-(2-chlorophenyl)ethanone (4 g, 13 mmol) and piperidine (5.8 g, 68 mmol) in 80% aqueous acetone (50 ml) is refluxed for 12 h. Additional portions of 0.3 g of piperidine are added three times in 4 h intervals to the mixture. The solvents are evaporated. Diethyl ether is added and the precipitated piperidine hydrochloride is filtered off. Diethyl ether is evaporated and the residual product is purified by flash chromatography (eluent toluene:triethylamine 9:1). The yield is 4.1 g, 89%.

$^1$H NMR (CDCl$_3$): 1.38–1.56 (m, 2H), 1.56–1.68 (m, 4H), 2.45–2.62 (m, 4H), 2.79 (t, 2H), 4.17 (t, 2H), 4.38 (s, 2H), 6.96 (d, 2H), 7.19–7.25 and 3.37–7.44 (2m, together 4H), 8.01 (d, 2H).

1-[4-(2-Imidazol-1-yl-ethoxy)phenyl]-2-phenyl Ethanone is prepared from 1-[4-(2-chloroethoxy)phenyl]-2-phenylethanone and imidazole in DMF using sodium hydride as a base according to the procedure described in the example 1a.

$^1$H NMR (CDCl$_3$): 4.22 (s, 2H), 4.20–4.37 (m, 4H), 6.88 (d, 2H), 7.03 (s, 1H), 7.07 (s, 1H), 7.20–7.37 (m, 5H), 7.60 (s, 1H), 7.97 (d, 2H).

c) 2-(2-Chlorophenyl-1-[4-(2-piperidinylethoxy) phenyl]-4-(tetrahydropyranyloxy)butan-1-one 2-(2-Chlorophenyl-1-[4-(2-piperidinylethoxy)phenyl]-4-(tetrahydropyranyloxy)butan-1-one is prepared by PTC reaction according to the method described in the example 4d using 2-(2-chlorophenyl)-1-[4-(2-piperidinylethoxy) phenyl]-ethanone (1.5 g, 4.2 mmol) and 2-tetrahydropyranyloxy-1-iodoethane (1.3 g, 5.1 mmol) as the starting materials. The product (1.6 g) is used for the following reaction step without further purification.

$^1$H NMR (CDCl$_3$): from the complex spectrum can be identified 2.40–2.60 (m, 4H), 2.75 (t, 2H), 4.12 (t, 2H), 4.50–4.62 (m, 1H), 5.24–5.36 (m, 1H), 6.87 (d, 2H), 7.10–7.25 and 3.37–7.44 (2m, together 4H), 7.98 (d, 2H).

Using the same method the following compound is prepared.

1-[4-(2-Imidazol-1-yl-ethoxy)phenyl]-2-phenyl-4-(tetrahydro-pyranyloxy)butan-1-one $^1$H NMR (CDCl$_3$): 1.4–1.9 (m, 6H), 1.95–2.2 (m, 1H), 2.4–2.60 (m, 1H), 3.2–3.9 (m, 4H), 4.2–4.37 (m, 4H), 4.45–4.55 (m, 1H), 4.79 (dt, 1H). 6.8 (dd, 2H), 6.99 (s, 1H), 7.05 (s, 1H), 7.15–7.3 (m, 5H), 7.55 (s, 1H), 7.95 (d, 2H).

d) 2-(2-Chlorophenyl-1-phenyl-1-[4-(2-piperidinylethoxy)phenyl]-4-(tetrahydropyranyloxy) butan-1-ol is prepared according to the procedure described in the example 4e. The product is used in the following reaction step without further purification.

Using the same method the following compounds are prepared:

1-[4-(2-Imidazol-1-yl-ethoxy)phenyl]-2-phenyl-4-(tetralhydro-pyranyloxy)-1-[3-(tetrahydro-pyranyloxy) phenyl]-butan-1-ol The compound is used in the next reaction step without further purification.

e) 3-(2-Chlorophenyl)-4-phenyl-4-[4-(2-piperidin-1-ylethoxy)phenyl]but-3-en-1-ol 2-(2-Chlorophenyl-1-phenyl-1-[4-(2-piperidinylethoxy) phenyl]-4-(tetrahydropyranyloxy)butan-1-ol is dehydrated according to the procedure described in the example 1c. The Z-isomer of the product is purified by flash chromatography (eluent toluene-triethylamine 13:1)

Z-isomer: ¹H NMR (CDCl₃): 1.35–1.48 (m, 2H), 1.48–1.68 (m, 4H), 2.38–2.48 (m, 4H), 2.66 (t, 2H), 2.58–2.87 (m, 2H), 3.47–3.67 (m, 2H), 3.94 (t, 2H), 6.54 (d,2H), 6.84 (d, 2H), 7.07–7.41 (m, 9H).

Using the same method the following compound is prepared.

3-{4-Hydroxy-1-[4-(2-imidazol-1-yl-ethoxy)pheny]-2-phenyl-but-1-enyl}-phenol

E-isomer: ¹NMR (CDCl₃+MeOH-d₄): 2.83 (t, 2H), 3.60 (t, 2H), 4.11 (dist.t, 2H), 4.20 (t, 2H), 6.48 (d, 2H), 6.76 (d, 2H), 6.66–6.9 (m, 4H), 6.92 (s, 1H), 6.98 (s, 1H), 7.08–7.32 (m, 5H), 7.36 (s, 1H).

Z-isomer: ¹H NMR (CDCl₃+MeOH-d₄): 2.73 (t, 2H). 3.54 (t, 2H), 4.23–4.4 (m, 4H), 6.35–7.23 (m, 15H), 7.55 (s, 1H).

f) (Z)-1-(2-{4-[4-Chloro-2-(2-chlorophenyl)-1-phenylbut-1-enyl]phenoxy}-ethyl)piperidine (No. 38)

is prepared according to the procedure described in the example 1d.

¹H NMR (CDCl3): 1.33–1.49 (m, 2H), 1.49–1.68 (m, 4H), 2.40–2.50 (m, 4H), 2.67 (t, 2H), 2.80–3.50 (m, 2H), 3.25–3.56 (m, 2H), 3.95 (t, 2H), 6.54 (d, 2H), 6.85 (d, 2H), 7.06–7.43 (m, 9H).

Using the same method the following compound included in the invention is prepared.

3-{4-Chloro-1-[4-(2-imidazol-1-yl-ethoxy)phenyl]-2-phenyl-but-1-enyl}-phenol (No. 39 and 40)

E-isomer (No. 39): ¹H NMR (CDCl₃): 2.94 (t, 2H), 3.41 (t, 2H). 4.07 (dist.t, 2H), 4.25 (t, 2H), 6.50 (d, 2H), 6.79 (d, 2H), 6.70–6.81 (m, 2H), 6.98 (s, 2H),7.10–7.24 (m, 7H), 7.51 (s, 1H).

Z-isomer (No. 40): ¹H NMR (CDCl₃+MeOH-d4, HCl-salt): 2.90 (dist.t, 2H), 3.40 (dist.t, 2H), 4.33 (dist.t, 2H), 4.65 (dist.t, 2H), 6.35–7.25 (m, 13H), 7.38 (s, 7.48 (s, 1H), 9.20 (s, 1H).

Example 6 a) (4-Amino-phenyl)phenyl-methanone

4-Nitrobenzophenonie (5.0 g, 0.022 mol) is dissolved in ethanol-dichloromethane (40 ml: 30 ml) and hydrogenated at room temperature with 10% palladium on carbon (0.5 g) as a catalyst. The catalyst is filtered off and the filtrate is evaporated to dryness. The product is used in the next reaction step without further purification. Yield 5.2 g.

¹H NMR (CDCl₃): 6.67 (d, 2H), 7.4–7.6 (m, 3H), 7.7–7.6 (m, 4H).

b) McMurry Reaction 4-(4-Chloro-1,2-diphenyl-but-1-enyl)phenylamine

Zinc (10.0 g, 0.154 mol) and tetrahydrofuran (THF) (120 ml) is added to the reaction vessel and cooled to –10° C. To the mixture is added dropwise titan tetrachloride (1 4.4 g, 0.076 mol) at about –10° C. After the addition is completed the mixture is refluxed for two hours. Then it is cooled to 40° C. and (4-Amino-phenyl)phenyl-methanone (5.1 g, 0.0258 mol) and 3-chloropropiophenone (4.36 g, 0.0258 mol) are dissolved in THF (50 ml) and added to the mixture. Refluxingis continued for additional 3.5 hours. The cooled reaction mixture is poured in aqueous potassium carbonate solution (14 g K₂CO₃+140 ml water) and allowed to stand over night. The mixture is filtered and the precipitate is washed three times with THF. The filtrate is evaporated to dryness. The residue is dissolved in ethyl acetate and washed with water. Yield 9.6 g Z-isomer being the only isomer.

Z-isomer: ¹H NMR (CDCl₃): 2.90 (t, 2H), 3.41 (t, 2H), 6.32 (d, 2H), 6.64 (d, 2H), 7.0–7.4 (m, 10H).

Using the same method the following compound included in the invention is prepared N-[4-(4-Chloro-1,2-diphenyl-but-1-enyl)-phenyl]-N',N'-dimethylethlane-1,2-diamine (No. 47)

starting from [4-(2-dimethylaminoethylamino)phenyl] phenyl methanone (preparation described in U.S. Pat. No. 5,693,674) and 3-chloropropiophenone.

Z-isomer: ¹H NMR (as HCl-salt, MeOH-d4): 2.95 (s, 6H), 2.99 (t, 2H), 3.44 (t, 2H), 3.47 (t, 2H), 3.68 (t, 2H), 6.90–7.10 (m, 4H), 7.15–7.40 (m, 10H).

c) (Z)-[4-(4-Chloro-1,2-diphenyl-but-1-enyl) phenylamino]acetic Acid Ethyl Ester (Z)-4-(4-Chloro-1,2-dipheinyl-but-1-enyl)phenylamine (2.0 g. 5.99 mmol), ethanol (30 ml), ethyl bromoacetate (2.5 g, 15 mmol) and sodium acetate (2.4 g. 17.9 mmol) are added to the reaction vessel and refluxed for three hours. Then the solvent is evaporated and the residue is dissolved in water and ethyl acetate. Ethyl acetate phase is dried and evaporated to dryness. Yield 2.9 g.

¹H NMR (CDCl₃): 1.26 (t, 3H), 2.90 (t, 211), 3.41 (t, 2H), 4.20 (q, 2H). 6.25 (d, 2H), 6.68 (d, 2H), 7.10–7.40 (m, 10H).

d) (Z)-2-[4-(4-Chloro-1,2-diphenyl-but-1-enyl) phenylamino]ethanol (No. 41)

(Z)-[4-(4-Chloro-1,2-diphenyl-but-1-enyl)phenylamino] acetic acid ethyl ester (2.9 g, 6.9 mmol) is dissolved in tetrahydrofuran and lithium aluminum hydride (0.34 g, 8.97 mmol) is added in small portions during fifteen minutes. The mixture is stirred at room temperature for two hours. Then the solvent is evaporated to dryness and the residue is dissolved in ethyl acetate and washed with water. Ethyl acetate phase is evaporated to dryness and the product is purified by flash chromatography with toluene:methanol:triethylamine solution (10:0.3:0.3) as an eluent. Yield 0.47 g.

¹H NMR (CDCl₃): 2.89 (t, 2H), 3.17 (t, 2H), 3.41 (t, 2H), 3.73 (t, 2H), 6.29 (d, 2H), 6.67 (d, 2H), 7.10–7.40 (m 10H).

Example 7 a) 4-{2-[4-(2-Benzyloxyethoxy)phenyl]-1-(2-chloroethyl)-2-phenylvinyl}phenol is prepared according to the method of example 6b using [(4-benzyloxyethoxy)-phenyl]phenylmethanone and 3-chloro-1-(4-hydroxyphenyl)propan-1-one as starting materials. The product is mixture of Z- and E-isomers.

¹H NMR (CDCl₃): 2.88 and 2.93 (2t, 2H), 3.42 and 3.43 (2t, 2H), 3.74 and 3.84 (2dist.t, 2H), 4.01 and 4.16 (2dist.t, 2H), 4.58 and 4.65 (2s, 2H), 6.55–7. 40 (m, 18H).

b) 4-{1-(2-Chloroethyl)-2-[4-(2-hydroxyethoxy) phenyl]-2-phenylvinyl}phenol (No. 42 and 43)

is prepared according to the procedure of the example 1e. The isomers are purified by flash chromatography (eluent dichloromethane-methanol-triethylamine 98:2:1)

Z-isomer (No. 42): ¹H NMR (CDCl₃): 2.87 (t, 2H), 3.43 (t, 2H), 3.83–3.90 (m, 2H), 3.90–3.97 (m, 2H), 6.56 (d, 2H), 6.66 (d, 2H), 6.80 (d, 2H), 6.96 (d, 2H), 7.20–7.40 (m, 5H).

E-isomer (No. 43): ¹H NMR (CDCl₃): 2.92 (t, 2H), 3.38 (t, 2H), 3.90–4.02 (m, 2H), 4.03–4.14 (m, 2H), 6.63 (d, 2H), 6.89 (d, 2H), 6.95 (d, 2H), 7.20 (d, 2H), 6.85–7.17 (m, 5H).

Example 8

{2-[4-(4-Chloro-1,2-diphenylbut-1-enyl)phenoxy]ethyl}methylprop-2-ynylamine (No. 44)

is prepared according to example 1a starting from Z-4-chloro-1,2-diphenyl-1[4-[2-(N-methylamino)ethoxy]-phenyl]-1-butene (preparation described in U.S. Pat. No. 5,491,173) and propargyl bromide.

$^1$H NMR (citrate salt, MeOH-d$_4$): 2.74 (s, 3H), 2.82 and 2.86 (2s, 4H), 2.93 (t, 2H), 3.06 (t, 1H), 3.29 (dist.t, 2H), 3.44 (t, 2H), 3.85 (d, 2H), 4.16 (dist.t, 2H), 6.68 (d, 2H), 6.86 (d, 2H), 7.15–7.47 (m, 10H).

Example 9 a) (Z)-[4-(4-Hydroxy-1,2-diphenylbut-1-enyl)phenyloxy]acetic acid ethyl ester is prepared from (Z)-(4-hydroxy-1,2-diphenylbut-1-enyl)phenol (preparation described in U.S. Pat. No. 4.996.225) and ethyl bromoacetate according to the procedure described in the example 1a using NaH as a base.

$^1$H NMR (CDCl$_3$): 1.25 (t, 3H), 2.74 (t, 2H), 3.57 (t, 2H), 4.23 (q, 2H), 4.47 (s, 2H), 6.56 (d, 2H), 6.79 (d, 2H), 7.10–7.45 (m, 10H).

(Z)-2-[4-(4-Hydroxy-1,2-diphenylbut-1-enyl)phenoxy]butyric acid ethyl ester is prepared according to the same procedure using ethyl 2-bromobutyrate as a alkylating reagent.

$^1$H NMR (MeOH-d$_4$): 0.98 (t, 3H), 1.17 (t, 3H), 1.86 (m, 2H), 2.70 (t, 2H), 3.47 (t, 2H), 4.12 (m, 2H), 4.50 (dd, 1H), 6.50 (d, 214), 6.76 (d, 2H), 7.0–7.4 (m, 10H).

b) (Z)-[4-(4-Chloro-1,2-diphenylbut-1-enyl]phenoxy)acetic acid ethyl ester is prepared according to procedure described in the example 1d using Ph$_3$P and CCl$_4$ as reagents.

$^1$H NMR (CDCl$_3$): 1.25 (t, 3H), 2.92 (t, 2H), 3.41 (t, 2H), 4.23 (q, 2H), 4.50 (s, 2H), 6.55 (d, 2H), 6.80 (d, 2H), 7.10–7.45 (m, 10H).

Using the same method the following compound is prepared (Z)-2-[4-(4-Chloro-1.2-diphenylbut-1-enyl)phenoxy]butyric acid ethyl ester $^1$H NMR (MeOH-d$_4$): 1.01 (t, 3H), 1.16 (t, 3H), 1.89 (m, 2H), 2.91 (t, 2H), 3.40 (t, 2H), 4.15 (m, 2H), 4.40 (dd, 1H), 6.52 (d, 2H), 6.76 (d, 2H), 7.0–7.4 (m, 10H).

c) (Z)-3-[4-(4-Chloro-1,2-diphenylbut-1-envl)phenoxymethyl]pentan-3-ol (No. 45)

Grignard reagent is prepared from Mg turnings (0.29 g, 12 mmol) and bromoethane (1.25 g, 12 mmol) in tetrahydrofuran (4 ml). (Z)-[4-(4-Chloro-1,2-diphenylbut-1-enyl)phenoxy)acetic acid ethyl ester (1.0 g, 23 mmol, from example 9b) in tetrahydrofuran (11 ml) is added in room temperature and the reaction mixture is refluxed for 2 h. Saturated ammonium chloride is added and tetrahydrofuran is evaporated. The product is extracted into ethyl acetate. The organic layer is dried and evaporated to dryness. The yield is 1.0 g.

$^1$H NMR (CDCl$_3$): 0.87 (t, 6H), 1.58 (q, 4H), 2.92 (t, 2H), 3.42 (t, 2H), 3.68 (s, 2H), 6.56 (d, 2H), 6.78 (d, 2H), 7.10–7.45 (m, 10H).

Example 10

(Z)-2-[4-(4-Chloro-1,2-diphenylbut-1-enyl)phenoxy]butan-1-ol (No. 46)

Z-2-[4-(4-Chloro-1,2-diplhenylbut-1-enyl)phenoxy]butyric acid ethyl ester (0.98 g, 2.2 mmol) is reduced by lithium aluminum hydride (0.041 g, 1.1 mmol) in tetrahydrofuran. Ice-water is added and tetrahydrofuran is evaporated. The product is extracted into ethyl acetate, dried and the solvent is evaporated. Yield 0.55 g.

$^1$H NMR (CDCl$_3$): 0.89 (t, 3H), 1.54–1.70 (m, 2H), 2.91 (t, 2H), 3.58–3.76 (m, 2H), 4.10–4.20 (m, 1H), 6.57 (d, 2H), 6.77 (d, 2H), 7.10–7.40 (m, 10H).

Example 11

E-3-(4-Chloro-1-{4-[2-(2-hydroxyethoxy)ethoxy]phenyl}-2-phenylbut-1-enyl)phenol a) 1-{4-[2-(2-Benzyloxyethoxy)ethoxy]phenyl}-2-phenyl ethanone is prepared according to example 4c starting from 1-(4-hydroxyphenyl)-2-phenyl ethanone (prepared according examples 4a–b)(10.0 g, 47.1 mmol) and 2-(2-benzyloxyethoxy)ethyl chloride (11.0 g, 51.8 mmol). The product was triturated three times with warm heptane to remove byproducts. Yield 9.6 g, 52%. $^1$H NMR (CDCl$_3$): 3.60–3.79 (m, 4H), 3.85 (dist.t, 2H), 4.16 (dist.t, 2H), 4.20 (s, 2H), 4.56 (s, 2H), 6.92 (d, 2H), 7.20–7.41 (m, 10H), 7.96 (d, 2H).

b) 1-{4-[2-(2-Benzyloxyethoxy)ethoxy]phenyl}-2-phenyl-4-(tetrahydropyran-2-yloxy)butan-1-one is prepared by using the method described in the example 4d starting from 1-{4-[2-(2-benzyloxyethoxy)ethoxy]phenyl}-2-phenylethanone (8.4g, 21.5 mmol) and 2-(tetrahydropyran-2-yloxy)ethyl iodide (6.6 g, 25.8 mmol). The product (11.7 g) is used in the next reaction step without further purification.

$^1$H NMR (CDCl$_3$): 1.40–1.95 (m, 6H), 2.00–2.20 and 2.40–2.60 (2m, together 2H), 3.60–3.80 (m, 8H), 3.83 (dist.t, 2H), 4.13 (dist.t, 2H), 4.45–4.55 (m, 1H), 4.55 (s, 2H), 4.80 (t, 1H), 6.86 (d, 2H), 7.14–7.39 (m, 10H), 7.96 (d, 2H).

c) 1-{4-[2-(2-Benzyloxyethoxy)ethoxy]phenyl}-2-phenyl-4-(tetrahydropyran-2-yloxy)-1-[3-(tetrahydropyran-2-yloxy)phenyl]butan-1-ol is prepared by using the method described in the example 4e starting from 1-{4-[2-(2-benzyloxyethoxy)ethoxy]phenyl}-2-phenyl-4-(tetrahydropyran-2-yloxy)butan-1-one (10 g, 19.2 mmol) and 3-(tetrahydropyran-2-yloxy)phenyl bromide (9.8 g, 38 mmol). The product is purified by flash chromatography with toluene-methanol (50:1) as eluent. Yield 5.7 g, 43%.

$^1$H NMR (CDCl$_3$): 1.40–2.20 (m, 10H), 3.5–4.1 (m, 14H), 4.30–4.50 (2m. 1H), 4.52 (s, 1H), 4.53 (s, 1H), 6.60 (d, 2H), 6.90–7.40 (m, 16H).

d) Z,E-3-(1-{4-[2-(2-Benzyloxyethoxy)ethoxy]phenyl}-4-hydroxy-2-phenylbut-1-enyl)phenol is prepared from 1-{4-[2-(2-benzyloxyethoxy)ethoxy]phenyl}-2-phenyl-4-(tetrahydropyran-2-yloxy)-1-[3-(tetrahydropyran-2-yloxy)phenyl]butan-1-ol (5.7 g, 8.2 mmol) by using the method described in the example 1c except that toluene is used instead of acetic anhydride (30 ml) and triethylamine (0.91 g, 0.9 mmol) is added. The product (3.8 g) is used in the next reaction step without further purification.

$^1$H NMR (CDCl$_3$): 2.78 (t, 2H), 3.55–4.20 (m, 10H), 4.55 and 4.58 (2s, 2H),6.56 (d, 2H), 6.73–6.93 (m, 3H), 7.1–7.4 (m, 13H).

e) Z,E-3-(1-{4-[2-(2-Benzyloxyethoxy)ethoxy]phenyl}-4-chloro-2-phenylbut-1-enyl)phenol is prepared from Z,E-3-(1-{4-[2-(2-benzyloxyethoxy)ethoxy]phenyl}-4-hydroxy-2-phenylbut-1-enyl)phenol (3.8 g, 7.4 mmol) by using the method described in example 4h except that triethylamine (1.64 g, 16.2 mmol) is added to the reaction mixture. The product is purified by flash chromatography. Yield 2.5 g.

$^1$H NMR (CDCl$_3$): 2.92 (t, 2H), 3.40 (t, 2H), 3.58–4.17 (m, 8H) 4.53 and 4.57 (2s, 2H), 6.53 (d, 2H), 6.71–6.9 (m, 6H), 7.1–7.4 (m, 10H).

f) E-3-(4-Chloro-1-{4-[2-(2-hydroxyethoxy)ethoxy]phenyl}-2-phenylbut-1-enyl)phenol Z,E-3-(1-{4-[2-(2-Benzyloxyethoxy)ethoxy]phenyl}-4-chloro-2-phenylbut-1-enyl)phenol (2.0 g, 3.78 mmol) is dissolved in ethyl acetate (30 ml). Zn (0.062 g, 0.95 mmol) and acetyl chloride (0.74 g, 9.5 mmol) are added under nitrogen atmosphere. The mixture is stirred at 50° C. for 3 h. The mixture is filtered and the solvent is evaporated. The residue is dissolved in 80% aqueous methanol containing 3% of sodium hydroxide. The mixture is stirred at room temperature for 2 h and methanol is evaporated. Water (5 ml) is added and the product is extracted into ethyl acetate (10 ml). The mixture is dried and the solvent is evaporated. The product is purified first by flash chromatography (eluent toluene:methanol 9:1) and then crystallized from toluene and recrystallized from toluene-acetone. Yield 0. 15 g.

$^1$H NMR (CDCl$_3$): 2.94 (t, 2H), 3.41 (t, 2H), 3.59–3.63 (m, 2H), 3.67–3.72 (m, 2H), 3.78 (dist.t, 2H), 4.01 (dist.t, 2H), 6.56 (d, 2H), 6.78 (d, 2H), 6.70–6.90 (m, 3H), 7.1–7.3 (m, 6H).

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications, patent applications and patents cited herein are fully incorporated by reference.

REFERENCES

Grodstein F, Stampfer M J: Estrogen for women at varying risk of coronary disease. Maturitas 30: 19–26. 1998.

Henderson V W: Estrogen, cognition, and a woman's risk of Alzheimer's disease. Am J Med 103(3A): 11S–18S, 1997.

Kangas L, Grönroos M, Nieminen A-L; Bioluminescence of cellular ATP: A new method for evaluating cytotoxic agents in vitro. Medical Biol 65: 338–343, 1984.

Kangas L, Nieminen A-L, Blanco G, Grönroos M, Kallio S, Karjalainen A, Perilä M, Södervall M, Toivola R: A new triphenylethylene compound, Fc-1157a. II. Antitumor effect. Cancer Chemother Pharmacol 17: 109–113, 1986.

Khovidhunkit W, Shoback D M: Clinical effects of raloxifene hydrochloride in women. Ann Intern Med 130(5): 431–439, 1999.

Lobo R A: Benefits and risks of estrogen replacement therapy. Am J Obstet Gynecol 173:982–990, 1995.

Macgregor J I, Jordan V C: Basic guide to the mechanism of antiestrogen action. Pharmnacol Rev 50:151–196, 1998.

Peng Z, Tuukkanen J, Zhang H, Jämsä T, Väänänen K: The mechanical strength of bone in different rat models of experimental osteoporosis. Bone 15: 523–532, 1994.

Terenius L: Structure-activity relationship of anti-oestrogens with regard to interaction with 17β-oestradiol in the mouse uterus and vagina. Acta Endocrinol 66: 431–447, 1971.

What is claimed is:

1. A compound of the formula:

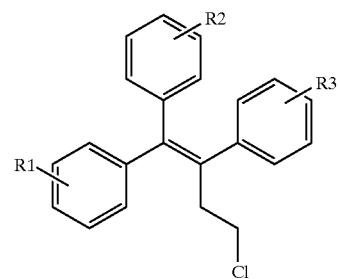

(I)

wherein

R1 is H, halogen, OCH$_3$, or OH;

R2 is b)

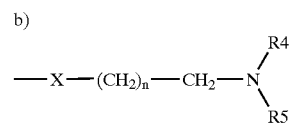

where X is O, and n is an integer from 1 to 4; and

R4 and R5, which are the same or different, are a 1 to 4 carbon alkyl, H, —CH$_2$C≡CH or —CH$_2$CH$_2$OH; or R4 and R5 form an N-containing five- or six-membered ring or heteroaromatic ring; and R3 is H, halogen, OH or —OCH$_3$;

or a stereoisomer; or a non-toxic pharmaceutically acceptable salt or ester thereof or mixtures thereof, provided that a) when R2 is

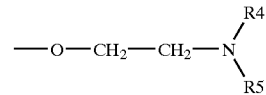

in the 4-position of the phenyl
where R4 and R5
  i) are the same, either methyl or ethyl; or
  ii) form an N-containing five-membered ring;
then R1 and R3 cannot simultaneously be H; and b) when R2 is

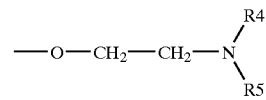

in the 4-position of the phenyl
where R4 and R5, which are the same or different, are methyl or H.

2. A compound according to claim 1 where n is 1, and R4 and R5 are methyl or form a piperidine or imidazole ring.

3. A compound according to claim 1, which is selected from the group consisting of
(2-{4-[4-chloro-1-(4-fluorophenyl)-2-phenylbut-1-enyl]phenoxy}ethyl)-dimethylamine,
(2-{4-[4-chloro-1-(4-chlorophenyl)-2-phenylbut-1-enyl]phenoxy}ethyl)-dimethylamine, (2-{4-[4-chloro-1,2-bis(4-chlorophenyl)but-1-enyl]phenoxy}ethyl)-dimethylamine, (2-{4-[4-chloro-2-(4-fluorophenyl)-1-phenylbut-1-enyl]phenoxy}ethyl)-dimethylaamine, (2-{4-[4-chloro-2-(4-chlorophenyl)-1-phenylbut-1-enyl]phenoxy}ethyl)-dimethylamine, (2-{4-[4-chloro-2-(4-chlorophenyl)-1-(4-methoxyphenyl)but-1-enyl]phenoxy}ethyl)dimethylamine, {2-[3-(4-chloro-1,2-diphenylbut-1-enyl)phenoxy]ethyl}dimethylamine, 1-{2-[4-(4-chloro-1,2-diphenyl-but-1-enyl)phenoxy]ethyl}-1H-imidazole, (2-[4-(4-chloro-1,2-diphenylbut-1-enyl)phenoxy]ethyl}methylprop-2-ynylamine, 2-({2-[4-(4-chloro-1,2-diphenyl-but-1-enyl)phenoxy]ethyl}methylamino)-ethanol, 3-{4-chloro-1-[4-(2-imidazol-1-yl-ethoxy)phenyl]-2-phenyl-but-1-enyl}-phenol, 1-(2-{4-[4-chloro-2-(2-chlorophenyl)-1-phenylbut-1-enyl]phenoxy}ethyl)-piperidine, 1-(2-{4-[4-chloro-2-(3-methoxyphenyl)-1-phenylbut-1-enyl]phenoxy}ethyl)-piperidine, and 1-(2-{4-[4-chloro-2-(2-methoxyphenyl)-1-phenylbut-1-enyl]phenoxy}ethyl)piperidine, or a stereoisomer; or a non-toxic pharmaceutically acceptable salt thereof.

4. A pharmaceutical composition comprising an amount effective to produce a tissue specific estrogenic and/or antiestrogenic effect of said selective estrogen receptor modulator compound according to claim 1, or a stereoisomer, or a non-toxic pharmaceutically acceptable salt or ester thereof, and a pharmaceutically compatible acceptable carrier therefor.

5. A method of producing a tissue specific estrogenic and/or antiestrogenic effect in a subject in which such an effect is desired which comprises administering to said subject said selective estrogen receptor modulator compound according to claim 1, a stereoisomer, or a non-toxic pharmaceutically acceptable salt or ester thereof in an amount sufficient to produce the desired effect.

6. A compound 2-(4-{4-chloro-1-[4-(2-hydroxyethoxy)phenyl]-2-phenyl-but-1-enyl}phenoxy)-1-ethanol, or a stereoisomer or a non-toxic pharmaceutically acceptable salt or ester thereof.

7. A pharmaceutical composition comprising an amount effective to produce a tissue specific estrogenic and/or antiestrogenic effect of said compound according to claim 6, or a stereoisomer, or a non-toxic pharmaceutically acceptable salt or ester thereof, and a pharmaceutically compatible acceptable carrier therefor.

8. A method of producing a tissue specific estrogenic and/or antiestrogenic effect in a subject in which such an effect is desired which comprises administering to said subject said compound according to claim 6, a stereoisomer, or a non-toxic pharmaceutically acceptable salt or ester thereof in an amount sufficient to produce the desired effect.

* * * * *

UNITED STATES PATENT AND TRADEMARK OFFICE
CERTIFICATE OF CORRECTION

PATENT NO. : 6,875,775 B2
DATED : February 25, 2005
INVENTOR(S) : Mandell et al.

It is certified that error appears in the above-identified patent and that said Letters Patent is hereby corrected as shown below:

Title page,
Item [60], Related U.S. Application Data, should read as follows:
-- [60] Provisional application No. 60/429,996, filed Nov. 29, 2002. --

Column 1,
Line 8, to read as follows: -- 60/429,996, filed Nov. 29, 2002, each entitled "Proximity" --

Column 10,
Line 2, to read as follows: -- hand-held appliance; and wherein --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO.     : 6,875,775 B2
DATED          : April 5, 2005
INVENTOR(S)    : Marja-Liisa Södervall et al.

It is certified that error appears in the above-identified patent and that said Letters Patent is hereby corrected as shown below:

This certificate supersedes Certificate of Correction issued May 31, 2005, the number was erroneously mentioned and should be vacated since no Certificate of Correction was granted.

Signed and Sealed this

Fifteenth Day of November, 2005

JON W. DUDAS
*Director of the United States Patent and Trademark Office*